United States Patent
Hamauzu et al.

(10) Patent No.: US 11,272,898 B2
(45) Date of Patent: Mar. 15, 2022

(54) RADIOGRAPHIC IMAGE PROCESSING APPARATUS, RADIOGRAPHIC IMAGE PROCESSING METHOD, AND RADIOGRAPHIC IMAGE PROCESSING PROGRAM

(71) Applicant: FUJIFILM CORPORATION, Tokyo (JP)

(72) Inventors: Shin Hamauzu, Kanagawa (JP); Ryoji Sasada, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 0 days.

(21) Appl. No.: 17/013,681

(22) Filed: Sep. 7, 2020

(65) Prior Publication Data
US 2021/0093280 A1 Apr. 1, 2021

(30) Foreign Application Priority Data
Sep. 27, 2019 (JP) .............................. JP2019-177642

(51) Int. Cl.
*A61B 6/00* (2006.01)
*H05G 1/44* (2006.01)

(52) U.S. Cl.
CPC ............ *A61B 6/5217* (2013.01); *A61B 6/462* (2013.01); *H05G 1/44* (2013.01); *A61B 6/4441* (2013.01)

(58) Field of Classification Search
None
See application file for complete search history.

(56) References Cited

U.S. PATENT DOCUMENTS 7,302,288 B1 * 11/2007 Schellenberg ......... A61B 90/36
                                                                600/427
2016/0317119 A1 * 11/2016 Tahmasebi Maraghoosh ..............
                                                                A61B 8/085
2020/0359977 A1 * 11/2020 Ogawa ..................... A61B 6/12

FOREIGN PATENT DOCUMENTS

JP     2017-202310 A    11/2017
JP     2018-517950 A     7/2018

* cited by examiner

*Primary Examiner* — Hoon K Song
(74) *Attorney, Agent, or Firm* — Solaris Intellectual Property Group, PLLC

(57) ABSTRACT

A detection unit detects a region of a surgical tool in a radiographic image of a patient. In a case in which the surgical tool is detected, a display control unit displays the radiographic image on a display unit such that the detected region of the surgical tool is highlighted.

11 Claims, 20 Drawing Sheets

RADIOGRAPHIC IMAGE PROCESSING APPARATUS, RADIOGRAPHIC IMAGE PROCESSING METHOD, AND RADIOGRAPHIC IMAGE PROCESSING PROGRAM

CROSS REFERENCE TO RELATED APPLICATIONS

The present application claims priority under 35 U.S.C. § 119 to Japanese Patent Application No. 2019-177642 filed on Sep. 27, 2019. The above application is hereby expressly incorporated by reference, in its entirety, into the present application.

BACKGROUND OF THE INVENTION

Technical Field

The present disclosure relates to a radiographic image processing apparatus, a radiographic image processing method, and a radiographic image processing program.

Related Art

Various surgical tools, such as gauze for suppressing bleeding, a thread and a needle for sewing up a wound, a scalpel and scissors for incision, a drain for draining blood, and forceps for opening incision, are used in a case in which a surgical operation is performed for a patient. The surgical tools may cause serious complications in a case in which they remain in the body of the patient after surgery. Therefore, it is necessary to check that no surgical tools remain in the body of the patient after surgery. However, there is a possibility that the remaining surgical tool will be overlooked by visual confirmation in an exhausted state after surgery.

Therefore, a method has been proposed which detects a foreign material in an image of a patient and displays the foreign material so as to be highlighted. For example, JP2017-202310A discloses a method that, in a case in which a foreign material, such as metal, is detected in a CT image of a patient, presents the detected foreign material on the image. Further, JP2018-517950A discloses a method that acquires a video image of a surgical site with a camera and displays a non-tissue region, such as gauze, in the video image so as to be highlighted.

However, CT images are not capable of being captured in an operating room and it is necessary to move a patient to an imaging room for CT imaging after surgery. Therefore, even in a case in which a foreign material is found in the body of the patient by the method described in JP2017-202310A, surgery needs to be performed again in order to remove the foreign material, which imposes a heavy burden on the patient. In addition, gauze is used to be pushed into the body of the patient and is stained with blood. Therefore, it is difficult to find gauze using the video image acquired by the camera as in the method described in JP2018-517950A. Further, in many cases, the surgical field is blocked by the operator. Therefore, it is difficult to always ensure the surgical field in order to acquire a video image. For this reason, there is a possibility that a surgical tool will remain in the body of the patient after the surgery in the method described in JP2018-517950A.

SUMMARY OF THE INVENTION

The present disclosure has been made in view of the above-mentioned problems and an object of the present disclosure is to provide a technique that can reliably prevent a surgical tool from remaining in a body of a patient after surgery, without imposing a burden on the patient.

According to the present disclosure, there is provided a radiographic image processing apparatus comprising: a detection unit that detects a region of a surgical tool in a radiographic image of a patient; and a display control unit that, in a case in which the surgical tool is detected, displays the radiographic image in which the detected region of the surgical tool has been highlighted on a display unit.

The "radiographic image" in the present disclosure means a two-dimensional image which is a fluoroscopic image of a subject acquired by irradiating the subject with radiation. The radiographic image may be a still image or a moving image. For example, the radiographic image may be acquired by a portable radiation detector. In some cases, the operator performs surgery while observing the radiographic image of the patient using a C-arm fluoroscopic apparatus. In this case, the radiographic image may be acquired by the C-arm fluoroscopic apparatus.

The radiographic image processing apparatus according to the present disclosure may further comprise an image processing unit that performs image processing for checking the surgical tool on the radiographic image to derive a processed radiographic image.

In the radiographic image processing apparatus according to the present disclosure, the radiographic image in which the detected region of the surgical tool has been highlighted and which is displayed on the display unit by the display control unit may be the processed radiographic image.

In the radiographic image processing apparatus according to the present disclosure, the display control unit may display, on the display unit, the radiographic image before the image processing for checking the surgical tool. The image processing unit may derive the processed radiographic image and the detection unit may start a process of detecting the region of the surgical tool in response to a command to detect the region of the surgical tool. In a case in which the processed radiographic image is derived, the display control unit may display the processed radiographic image on the display unit, instead of the radiographic image before the image processing or together with the radiographic image before the image processing. After the process of detecting the region of the surgical tool ends, the display control unit may display the radiographic image in which the region of the surgical tool has been highlighted on the display unit.

In the radiographic image processing apparatus according to the present disclosure, the display control unit may further display the radiographic image in which the detected region of the surgical tool has been highlighted on another display unit that has a larger size and/or a higher resolution than the display unit.

In the radiographic image processing apparatus according to the present disclosure, the display control unit may further display the radiographic image before the image processing, the processed radiographic image, and the radiographic image in which the detected region of the surgical tool has been highlighted on another display unit that has a larger size and/or a higher resolution than the display unit.

In the radiographic image processing apparatus according to the present disclosure, in a case in which the surgical tool is not detected, the display control unit may notify the fact.

In the radiographic image processing apparatus according to the present disclosure, the radiographic image may be acquired by a portable radiation detector or an imaging apparatus that is installed in an operating room for performing surgery on the patient.

In the radiographic image processing apparatus according to the present disclosure, the detection unit may include a discriminator trained so as to discriminate the region of the surgical tool in an input radiographic image.

In the radiographic image processing apparatus according to the present disclosure, the surgical tool may include at least one of gauze, a scalpel, scissors, a drain, a needle, a thread, or forceps.

In the radiographic image processing apparatus according to the present disclosure, at least a portion of the gauze may include a radiation absorbing thread.

According to the present disclosure, there is provided a radiographic image processing method comprising: detecting a region of a surgical tool in a radiographic image of a patient; and in a case in which the surgical tool is detected, displaying the radiographic image on a display unit such that the detected region of the surgical tool is highlighted.

In addition, a program that causes a computer to perform the radiographic image processing method according to the present disclosure may be provided.

Another radiographic image processing apparatus according to the present disclosure comprises a memory that stores commands to be executed by a computer and a processor that is configured to execute the stored commands. The processor performs: a process of detecting a region of a surgical tool in a radiographic image of a patient; and a process of, in a case in which the surgical tool is detected, displaying the radiographic image on a display unit such that the detected region of the surgical tool is highlighted.

According to the present disclosure, it is possible to reliably prevent a surgical tool from remaining in a body of a patient after surgery, without imposing a burden on the patient.

DETAILED DESCRIPTION

Figure 1:
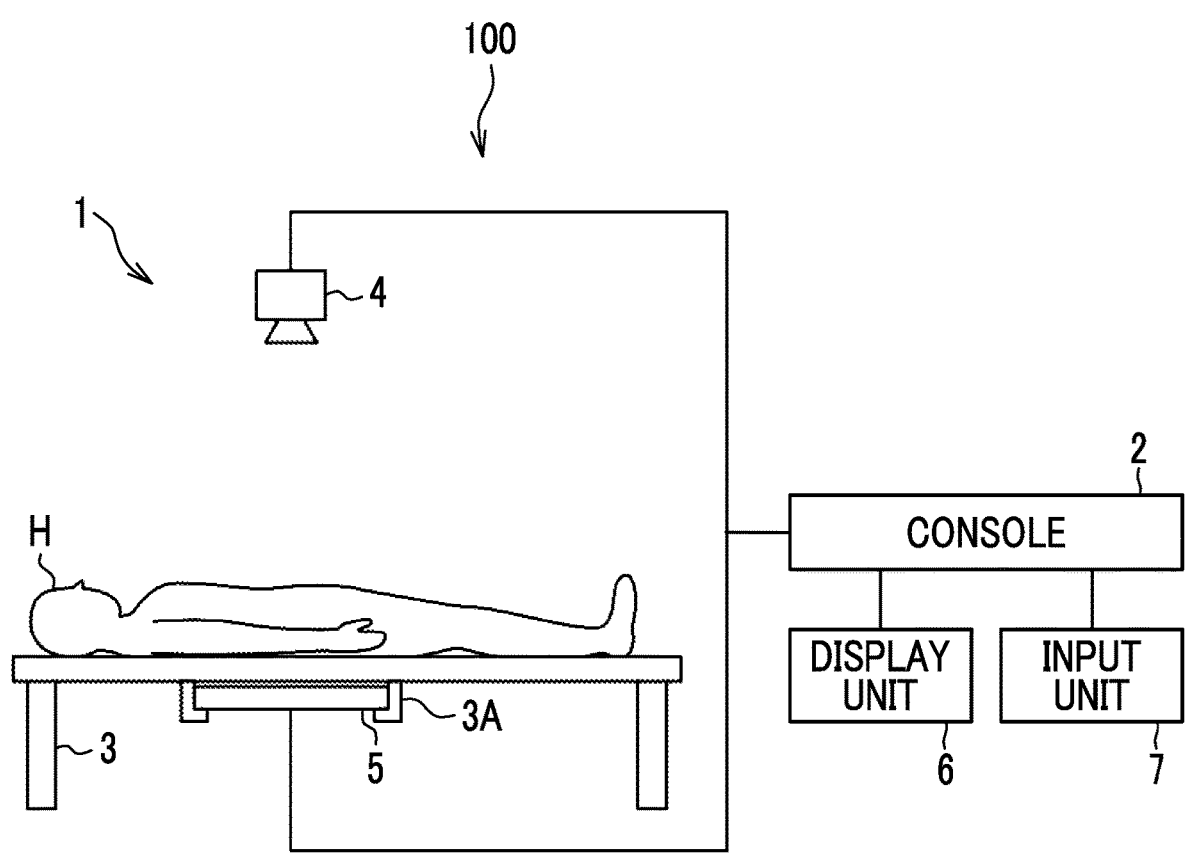
FIG. 1 is a block diagram schematically illustrating a configuration of a radiography system to which a radiographic image processing apparatus according to a first embodiment of the present disclosure is applied.

Hereinafter, embodiments of the present disclosure will be described with reference to the drawings. FIG. 1 is a block diagram schematically illustrating a configuration of a radiography system to which a radiographic image processing apparatus according to a first embodiment of the present disclosure is applied. As illustrated in FIG. 1, a radiography system 100 according to the first embodiment acquires a radiographic image of a subject as a patient after a surgical operation and detects a surgical tool included in the radiographic image. The radiography system 100 according to this embodiment comprises an imaging apparatus 1 and a console 2 which is the radiographic image processing apparatus according to this embodiment.

The imaging apparatus 1 irradiates a radiation detector 5 with radiation which has been emitted from a radiation source 4, such as an X-ray source, and transmitted through a subject H to acquire a radiographic image G0 of the subject H that lies supine on an operating table 3. The radiographic image G0 is input to the console 2 which is the radiographic image processing apparatus.

The radiation detector 5 can repeatedly perform the recording and reading of a radiographic image and may be a so-called direct-type radiation detector that directly receives the emitted radiation and generates charge or a so-called indirect-type radiation detector that converts radiation into visible light and then converts the visible light into a charge signal. As a method for reading a radiographic image signal, it is desirable to use a so-called thin film transistor (TFT) reading method which turns on and off a TFT switch to read a radiographic image signal or a so-called optical reading method which emits reading light to read a radiographic image signal. However, the present disclosure is not limited thereto and other methods may be used.

The radiation detector 5 is a portable radiation detector and is attached to the operating table 3 by an attachment portion 3A that is provided in the operating table 3. The radiation detector 5 may be fixed to the operating table 3.

A display unit 6 and an input unit 7 are connected to the console 2. The display unit 6 consists of display, for example, a cathode ray tube (CRT) or a liquid crystal display and assists the input of a radiographic image acquired by imaging and various kinds of data necessary for processes performed by the computer 2. The input unit 7 consists of, for example, a keyboard, a mouse, or a touch panel.

A radiographic image processing program according to this embodiment is installed in the console 2. In this embodiment, the console 2 may be a workstation or a personal computer that is directly operated by an operator or a server computer that is connected to the console through a network. The radiographic image processing program is stored in a storage device of the server computer connected to the network or a network storage so as to be accessed from the outside and is downloaded and installed in the computer on demand. Alternatively, the radiographic image processing program is recorded on a recording medium such as a digital versatile disc (DVD) or a compact disc read only memory (CD-ROM), is distributed, and is installed in the computer from the recording medium.

Figure 2:
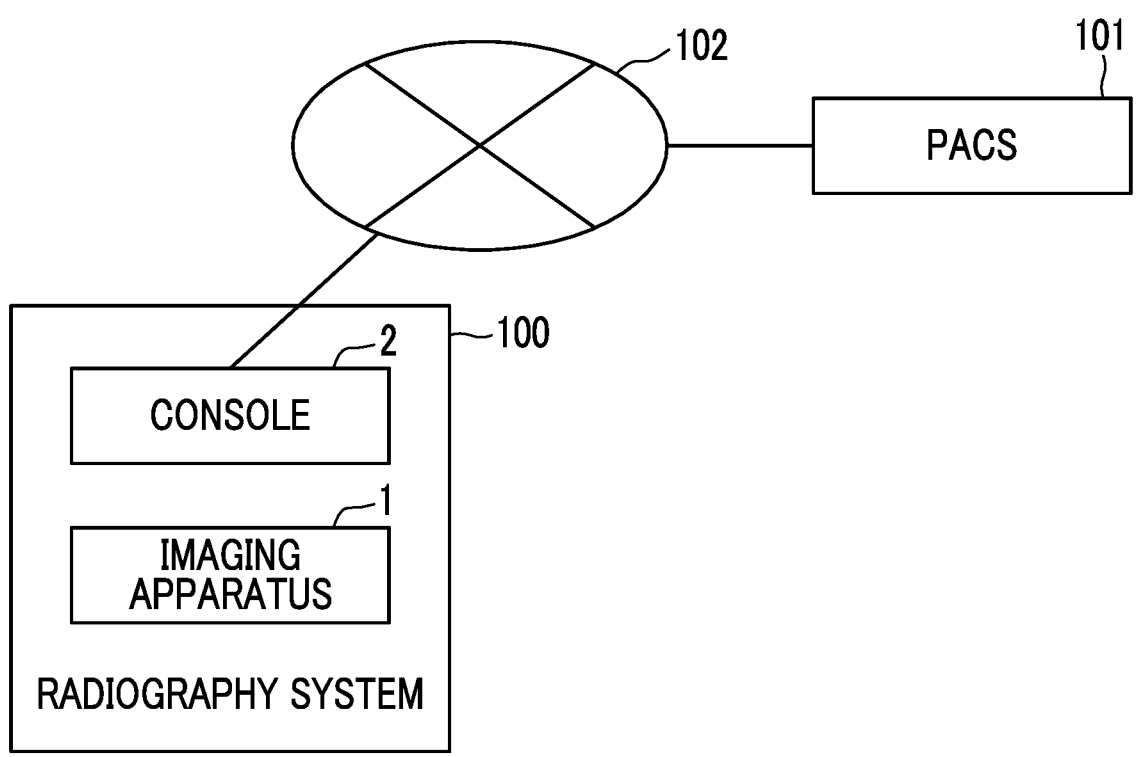
FIG. 2 is a block diagram schematically illustrating a configuration of a radiographic image management system.

The radiography system according to this embodiment forms a portion of a radiographic image management system illustrated in FIG. 2. As illustrated in FIG. 2, in the radiographic image management system according to this embodiment, the radiography system 100 including the imaging apparatus 1 and the console 2 and a picture archiving and communication system (PACS) 101 are connected through a network 102 such that they can communicate with each other.

Figure 3:
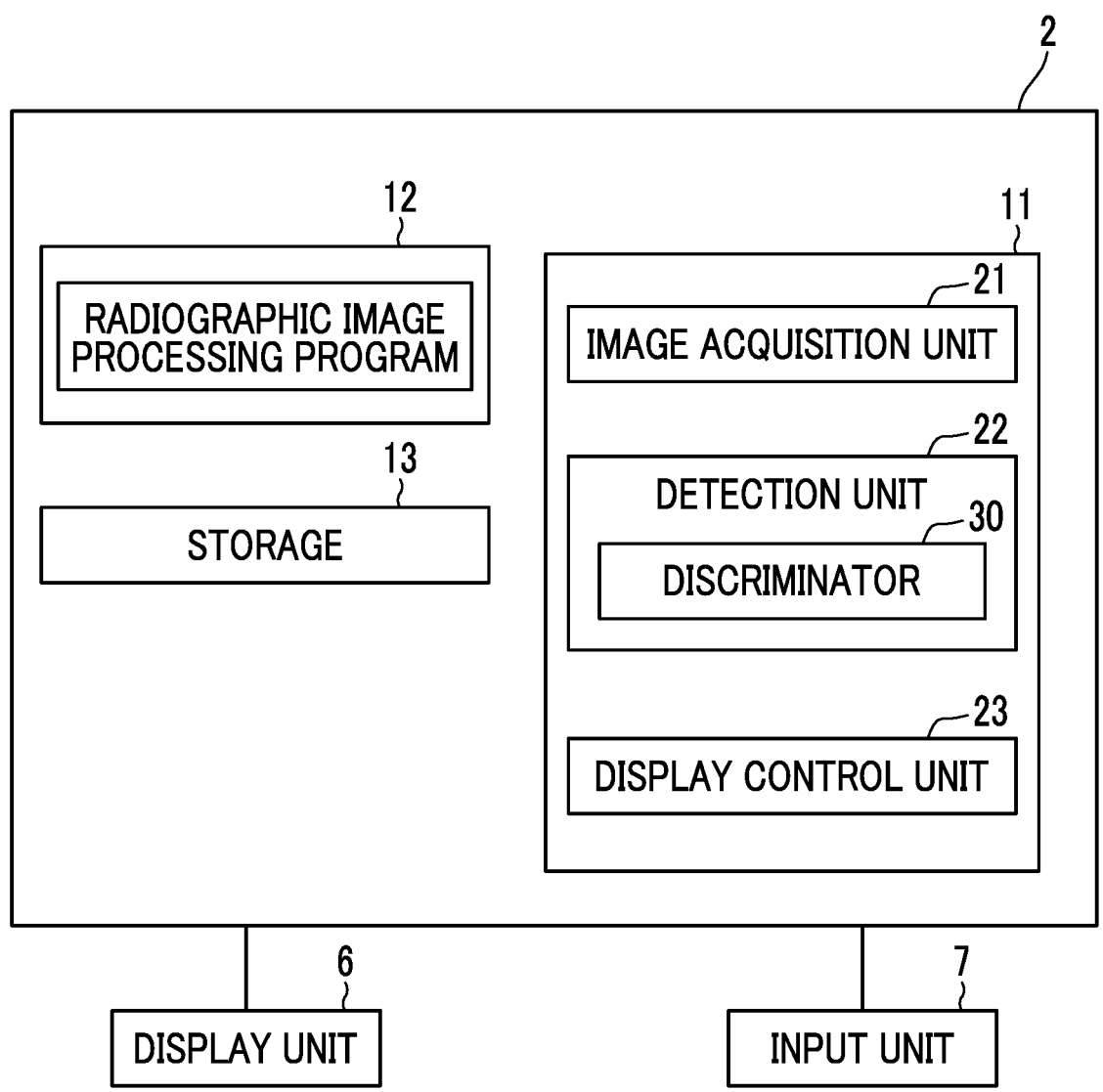
FIG. 3 is a diagram schematically illustrating a configuration of the radiographic image processing apparatus according to the first embodiment.

FIG. 3 is a diagram schematically illustrating the configuration of the radiographic image processing apparatus implemented by installing, for example, the radiographic image processing program according to the first embodiment in the console 2. As illustrated in FIG. 3, the radiographic image processing apparatus comprises a central processing unit (CPU) 11, a memory 12, and a storage 13 as a standard computer configuration.

The storage 13 consists of a storage device, such as a hard disk or a solid state drive (SSD), and stores various kinds of information including an imaging program for driving each unit of the imaging apparatus 1 and the radiographic image processing program. In addition, the radiographic image acquired by imaging is stored in the storage 13.

The memory 12 temporarily stores, for example, the radiographic image processing program stored in the storage 13 in order to cause the CPU 11 to perform various processes. The radiographic image processing program defines the following processes as processes to be performed by the CPU 11: an image acquisition process that irradiates the radiation detector 5 with radiation, which has been emitted from the radiation source 4 and then transmitted through the subject H, to acquire the radiographic image G0; a detection process that detects a region of a surgical tool in the radiographic image; and a display control process that displays the radiographic image on the display unit 6 such that the detected region of the surgical tool is highlighted in a case in which the surgical tool is detected.

The CPU 11 performs the above-mentioned processes according to the radiographic image processing program such that the console 2 functions as an image acquisition unit 21, a detection unit 22, and a display control unit 23.

The image acquisition unit 21 drives the radiation source 4 to irradiate the subject H that has undergone surgery with radiation and detects the radiation transmitted through the subject H using the radiation detector 5 to acquire the radiographic image G0. In this case, the image acquisition unit 21 sets imaging conditions, such as the type of target and filter used in the radiation source 4, an imaging dose, a tube voltage, and a SID.

The detection unit 22 detects the region of the surgical tool in the radiographic image G0. For the detection, a discriminator 30 that discriminates the region of the surgical tool included in the radiographic image G0 in a case in which the radiographic image G0 is input is applied to the detection unit 22. In a case in which the target radiographic image G0 is input to the detection unit 22, the detection unit 22 directs the discriminator 30 to discriminate the region of the surgical tool included in the radiographic image G0, thereby detecting the region of the surgical tool.

Here, the discriminator 30 is constructed by training a machine learning model using a radiographic image including a surgical tool as training data. In this embodiment, it is assumed that gauze is used as the surgical tool.

Figure 4:
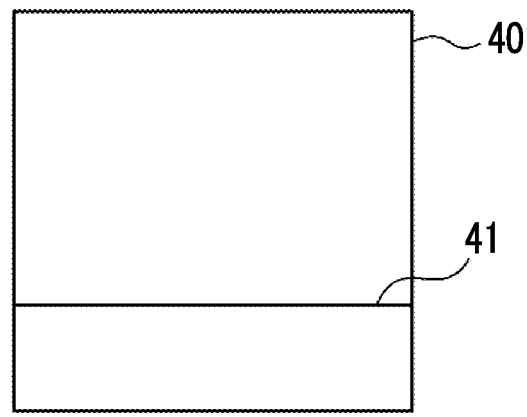
FIG. 4 is a diagram illustrating gauze.
Figure 5:
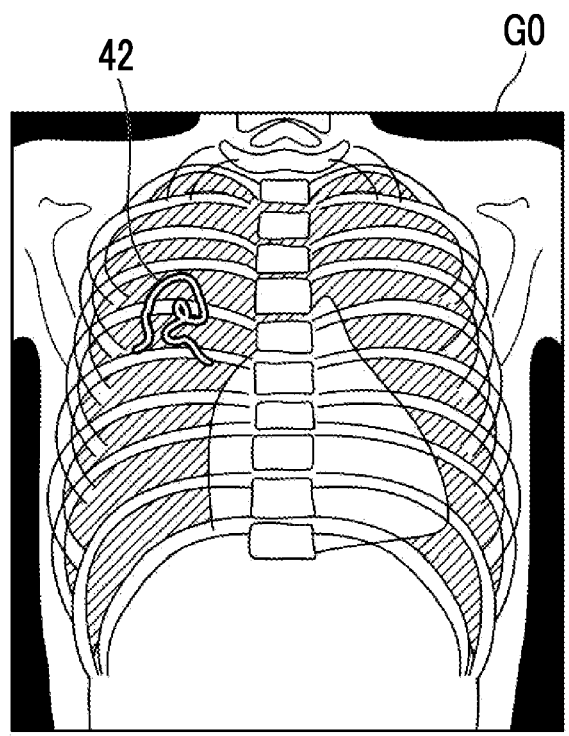
FIG. 5 is a diagram illustrating a radiographic image including a surgical tool.

FIG. 4 is a diagram illustrating gauze. As illustrated in FIG. 4, gauze 40 is a plain-woven cotton fabric and a radiation absorbing thread 41 is woven in a portion of the gauze 40. Cotton yarn transmits radiation and the radiation absorbing thread 41 absorbs radiation. Therefore, the radiographic image of the gauze 40 includes only the linear radiation absorbing thread 41. Here, during surgery, the gauze 40 is rolled and inserted into the human body in order to absorb blood. Therefore, in a case in which the gauze 40 is present in the human body, as illustrated in FIG. 5, a gauze image 42 which is the image of the gauze 40 included in the radiographic image G0 represents a state in which the radiation absorbing thread 41 is curled.

Figure 6:
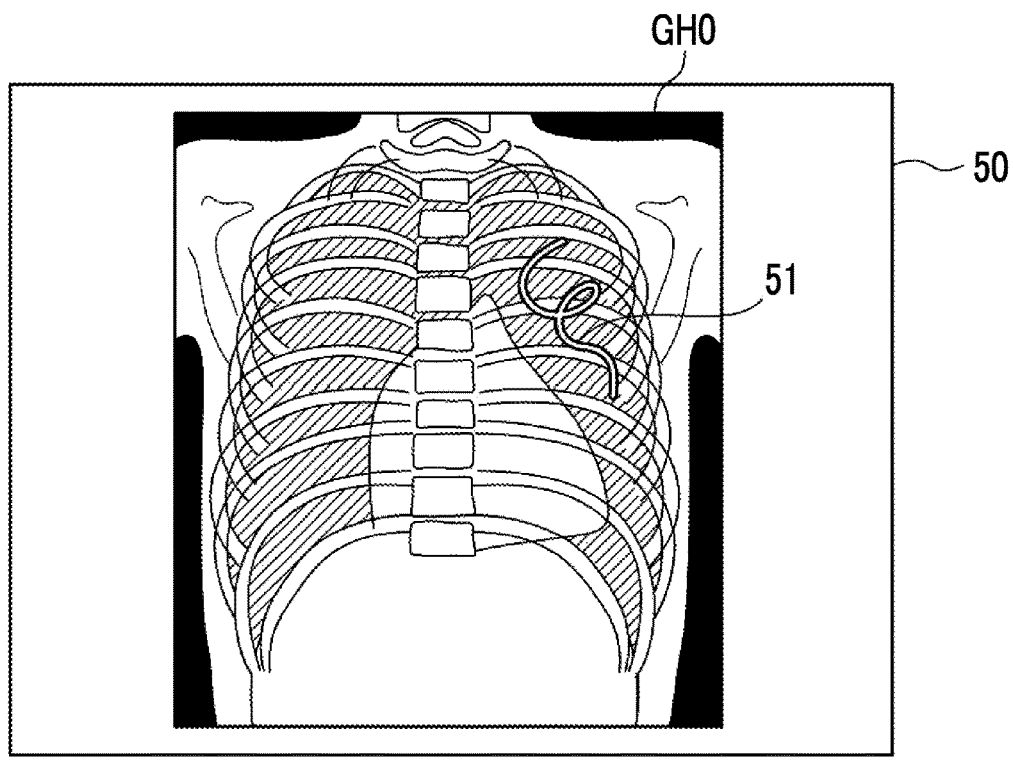
FIG. 6 is a diagram illustrating a display screen for a radiographic image in which a region of a surgical tool is highlighted.
Figure 7:
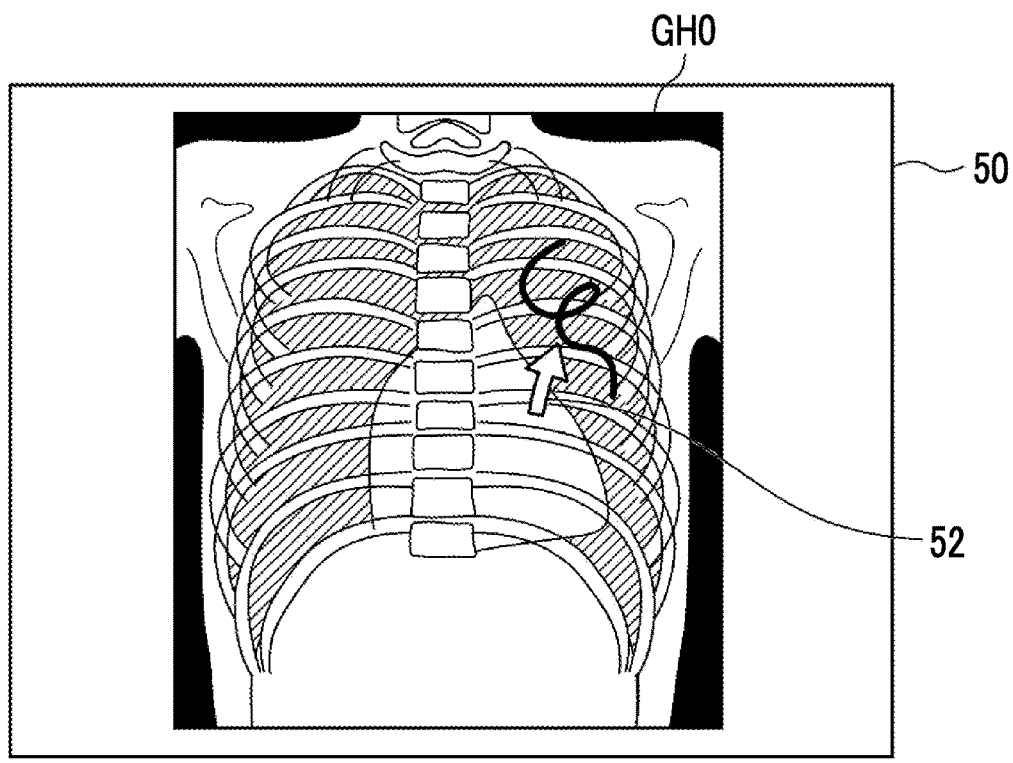
FIG. 7 is a diagram illustrating the display screen for the radiographic image in which the region of the surgical tool is highlighted.
Figure 8:
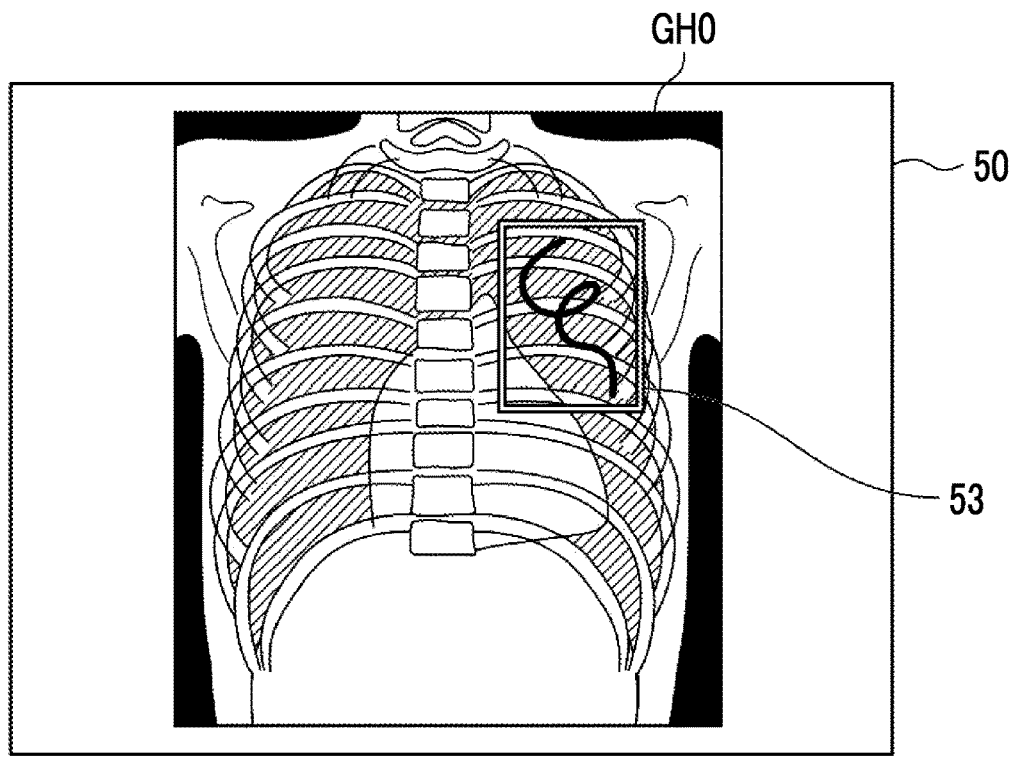
FIG. 8 is a diagram illustrating the display screen for the radiographic image in which the region of the surgical tool is highlighted.

In a case in which the detection unit 22 detects the region of the surgical tool from the radiographic image G0, the display control unit 23 displays the radiographic image G0 on the display unit 6 such that the region of the surgical tool is highlighted. FIG. 6 is a diagram illustrating a display screen for a radiographic image in which the region of the surgical tool is highlighted. As illustrated in FIG. 6, a radiographic image GH0 obtained by superimposing a mask 51 on the region of the surgical tool included in the radiographic image G0 such that the region of the surgical tool is highlighted is displayed on a display screen 50. The mask 51 is illustrated in white in FIG. 6. However, the mask 51 may be colored. Further, the region of the surgical tool may be highlighted by superimposing a mark 52, such as an arrow or an asterisk, in the vicinity of the region of the surgical tool as illustrated in FIG. 7 or by surrounding the region of the surgical tool with a frame 53 as illustrated in FIG. 8, instead of adding the mask 51. Here, the radiographic image GH0 in which the region of the surgical tool has been highlighted may be displayed on the display unit 6 by superimposing the mask 51, the mark 52, and the frame 53 (hereinafter, referred to as a mask and the like) on the radiographic image G0. In addition, a process of adding the mask or the like may be performed on the radiographic image G0 to separately generate the radiographic image GH0 in which the region of the surgical tool has been highlighted and the radiographic image GH0 may be displayed on the display unit 6.

In addition, in a case in which the radiographic image GH0 in which the region of the surgical tool has been highlighted is displayed on the display unit 6, image processing for display, such as a gradation conversion process or a density conversion process, may be performed on the radiographic image G0 in order for the operator to easily observe the displayed radiographic image GH0. The display control unit 23 may perform the image processing for display or an image processing unit for performing the image processing for display may be separately provided. In a case in which the image processing for display is performed on the radiographic image G0, the detection unit 22 may detect the region of the surgical tool from the radiographic image G0 subjected to the image processing for display.

Figure 9:
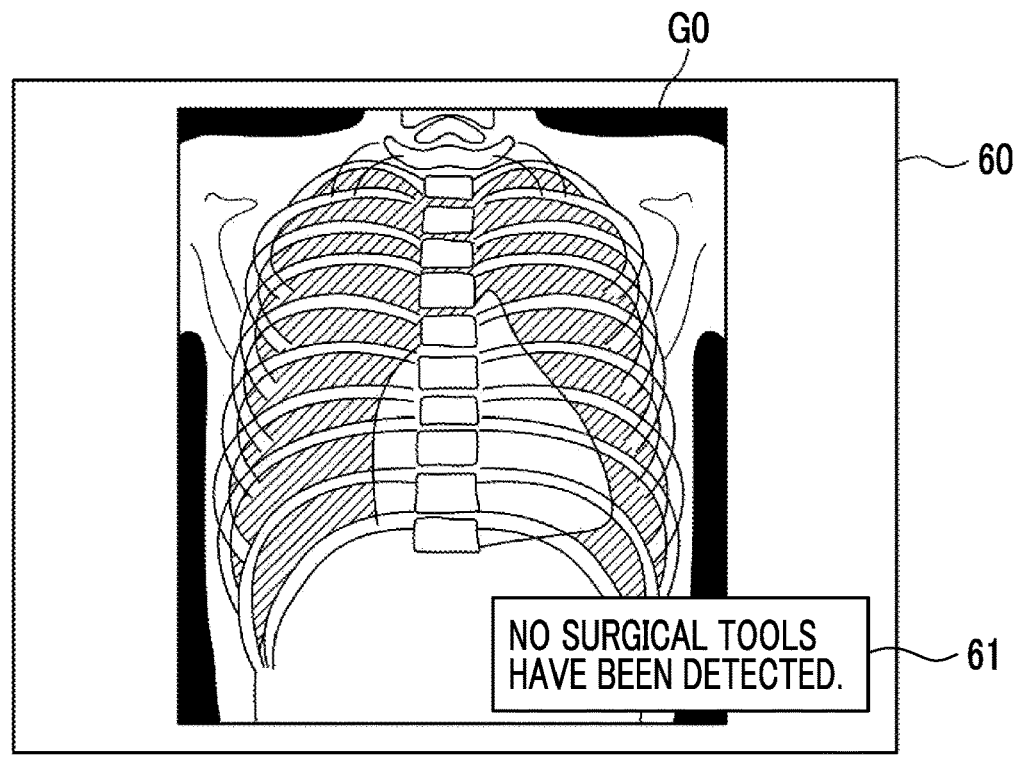
FIG. 9 is a diagram illustrating a notification screen in a case in which the region of the surgical tool is not detected.

In addition, in a case in which the detection unit 22 does not detect the region of the surgical tool from the radiographic image G0, the display control unit 23 notifies the fact. FIG. 9 is a diagram illustrating a notification screen in a case in which no surgical tools are detected. As illustrated in FIG. 9, a message 61 of "No surgical tools have been detected." is displayed on a notification screen 60 so as to be superimposed on the radiographic image G0. Instead of the message 61, for example, an icon or a mark indicating that no surgical tools have been detected may be displayed. Further, the turn-on and turn-off the display of the message 61 may be switched in response to a command from the input unit 7.

Figure 10:
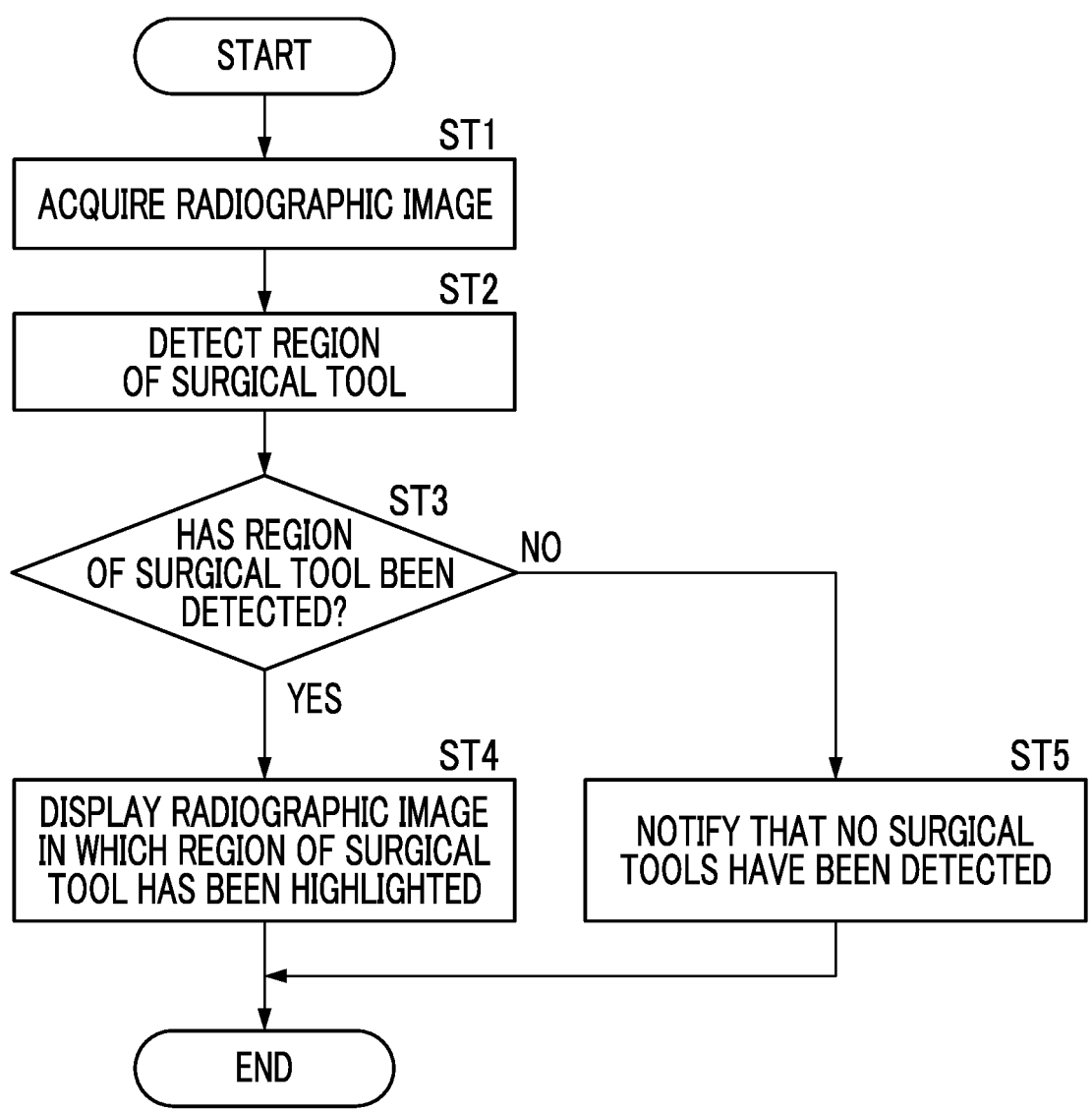
FIG. 10 is a flowchart illustrating a process performed in the first embodiment.

Next, a surgical tool region detection process according to the first embodiment will be described. FIG. 10 is a flowchart illustrating the detection process performed in the first embodiment. The image acquisition unit 21 acquires the radiographic image G0 as a detection target (Step ST1) and the detection unit 22 detects a region of a surgical tool from the radiographic image G0 (Step ST2).

Then, the display control unit 23 determines whether or not the region of the surgical tool has been detected from the radiographic image G0 (Step ST3). In a case in which the determination result in Step ST3 is "Yes", the display control unit 23 displays the radiographic image G0 in which the region of the surgical tool has been highlighted on the display unit 6 (the display of the radiographic image in which the surgical tool has been highlighted; Step ST4). Then, the process ends. On the other hand, in a case in which the determination result in Step ST3 is "No", the display control unit 23 notifies that the region of the surgical tool has not been detected (notification that the surgical tool has not been detected; Step ST5). Then, the process ends.

As described above, in the first embodiment, in a case in which the region of the surgical tool is detected in the radiographic image G0 of the patient, the radiographic image G0 is displayed such that the detected region of the surgical tool is highlighted. Here, the radiographic image G0 can be acquired in a state in which the patient is in the operating room. Further, since the radiographic image G0 is a fluoroscopic image, it is easy to detect the surgical tool buried in the surgical field, as compared to an image acquired by a camera. Therefore, according to this embodiment, it is possible to reliably prevent a surgical tool from remaining in the body of the patient after surgery, without imposing a burden on the patient.

Further, in the first embodiment, in a case in which the region of the surgical tool is not detected in the radiographic image G0, the fact is notified. Therefore, the operator can recognize that no surgical tools remain in the body of the patient.

Figure 11:
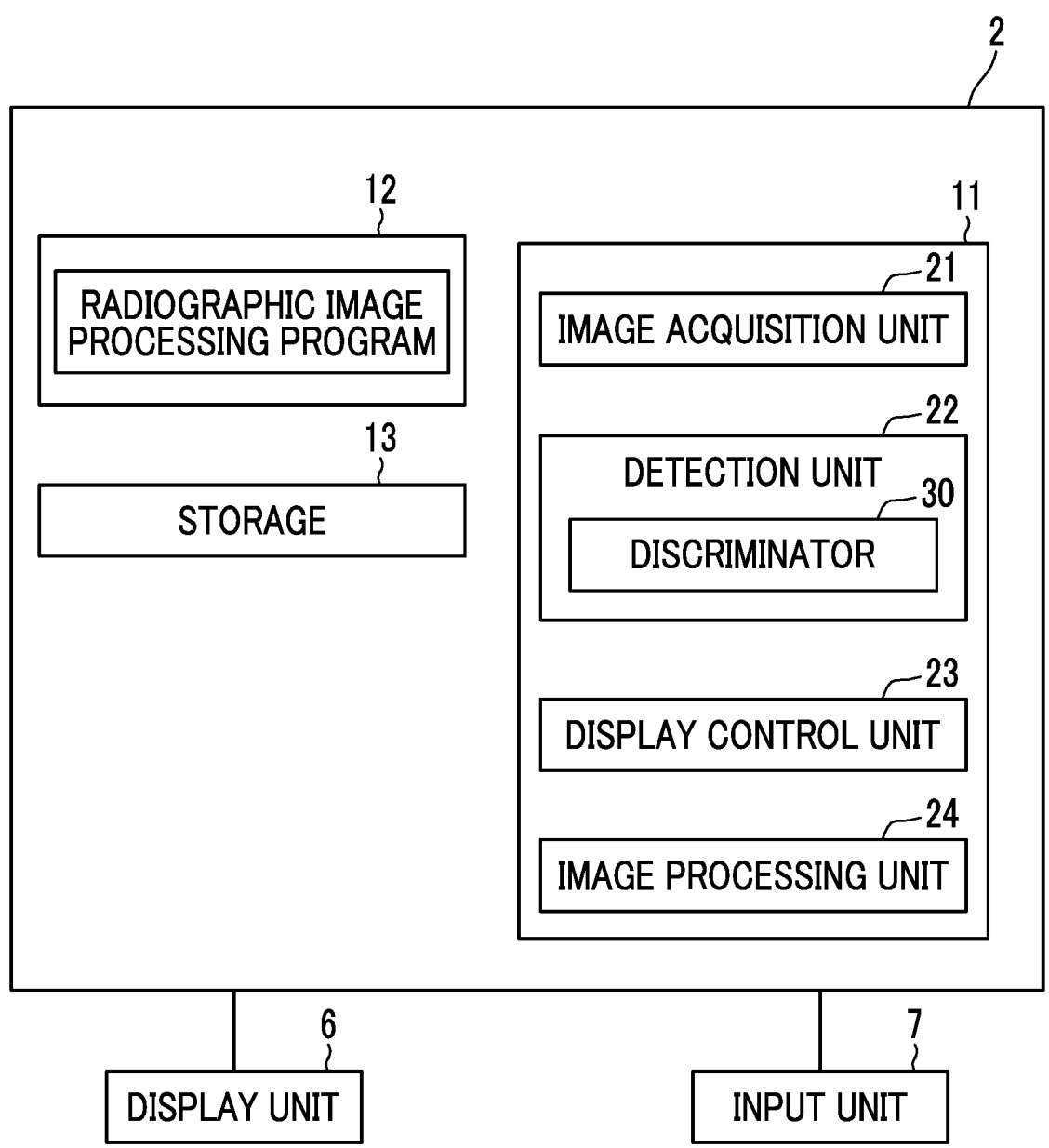
FIG. 11 is a diagram schematically illustrating a configuration of a radiographic image processing apparatus according to a second embodiment.

Next, a second embodiment of the present disclosure will be described. FIG. 11 is a diagram schematically illustrating the configuration of a radiographic image processing apparatus according to the second embodiment implemented by installing, for example, a radiographic image processing program according to the second embodiment in the console 2. In FIG. 11, the same components as those in FIG. 3 are denoted by the same reference numerals and the detailed description thereof will be repeated. As illustrated in FIG. 11, the radiographic image processing apparatus according to the second embodiment differs from the radiographic image processing apparatus according to the first embodiment in that it comprises an image processing unit 24 that performs image processing for checking a surgical tool on the radiographic image G0 to derive a processed radiographic image G1.

The image processing unit 24 performs the image processing for checking a surgical tool on the radiographic image G0. Examples of the image processing for checking a surgical tool include a process that emphasizes the sharpness of the radiographic image G0 and a gradation conversion process that converts the gradation of the radiographic image G0 in order to eliminate a blocked-up shadow in which a high-density component is saturated and a blown-out highlight in which a low-density component is saturated in the radiographic image G0.

In addition, in the second embodiment, the detection unit 22 may detect the region of the surgical tool from the radiographic image G0 or may detect the region of the surgical tool from the processed radiographic image G1. Here, it is assumed that the region of the surgical tool is detected from the radiographic image G0.

Figure 12:
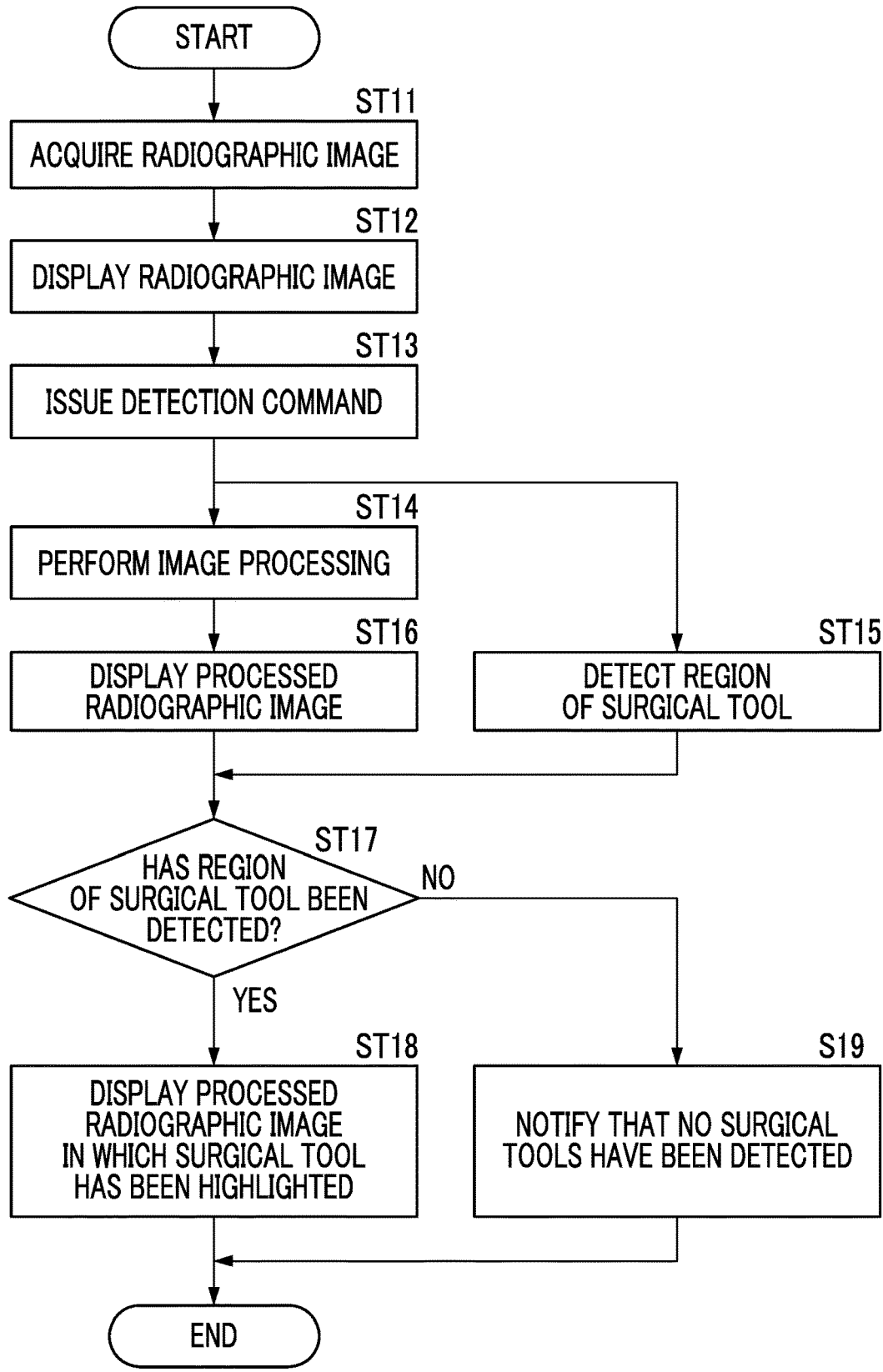
FIG. 12 is a flowchart illustrating a processing performed in the second embodiment.
Figure 13:
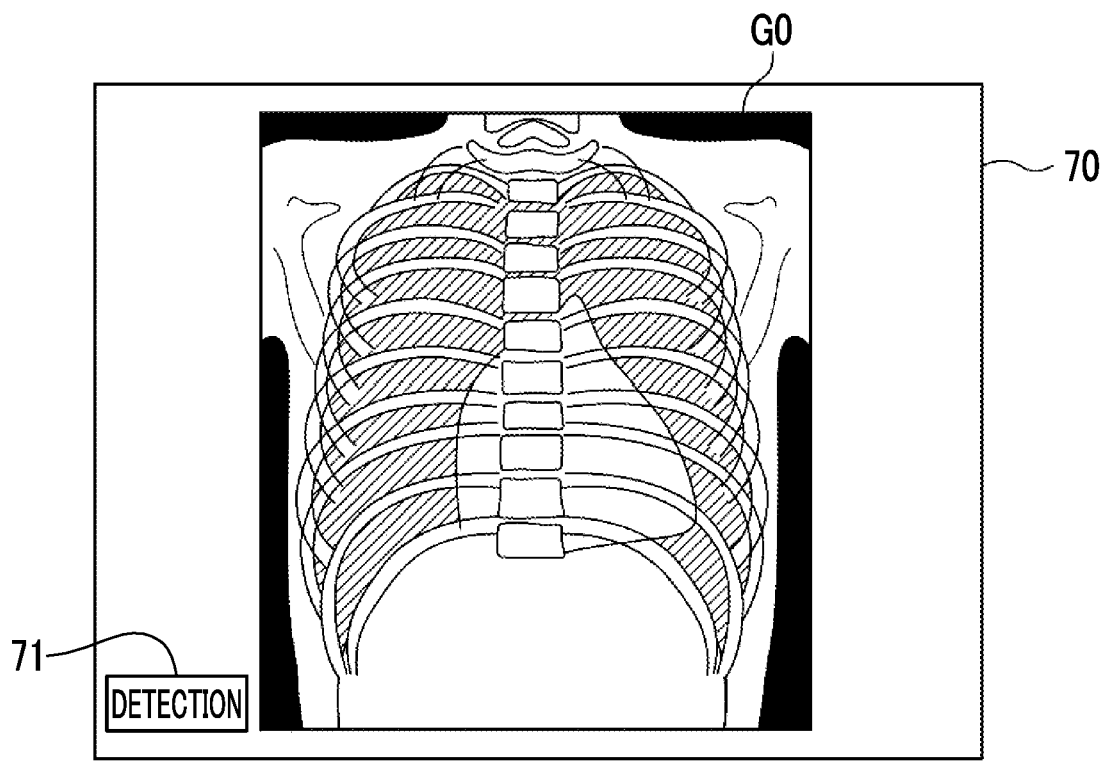
FIG. 13 is a diagram illustrating a radiographic image display screen.

In addition, in the second embodiment, the radiographic image G0 and the processed radiographic image G1 are displayed as follows. FIG. 12 is a flowchart illustrating a process performed in the second embodiment. The image acquisition unit 21 acquires the radiographic image G0 as a detection target (Step ST11) and the display control unit 23 displays the radiographic image G0 on the display unit 6 (Step ST12). FIG. 13 is a diagram illustrating a display screen for the radiographic image G0. As illustrated in FIG. 13, the radiographic image G0 is displayed on a display screen 70. Further, a detection button 71 for receiving a command to detect the region of the surgical tool is displayed on the display screen 70. In addition, image processing for display may be performed on the radiographic image G0. Further, in a case in which the radiographic image G0 includes the region of the surgical tool, the region of the surgical tool may be checked in the displayed radiographic image G0. However, in FIG. 13, the region of the surgical tool is not included in the radiographic image G0.

Next, in a case in which the detection button 71 is selected and a command to detect the surgical tool is input from the input unit 7 (Step ST13), the image processing unit 24 performs image processing for checking a surgical tool on the radiographic image G0 (Step ST14). Further, the detection unit 22 detects the region of the surgical tool from the radiographic image G0 in response to the detection command (Step ST15). After the image processing for checking a surgical tool, the display control unit 23 displays the processed radiographic image G1 on the display unit 6 (Step ST16). The process in Step ST15 is performed in parallel to the processes in Steps ST14 and ST16. However, the process in Step ST15 may be performed after Step ST14 or Step ST16. In a case in which the region of the surgical tool is detected from the processed radiographic image G1, the process in Step ST15 may be performed in parallel to the process in Step ST16 after Step ST14 or may be performed after Step ST16.

Figure 14:
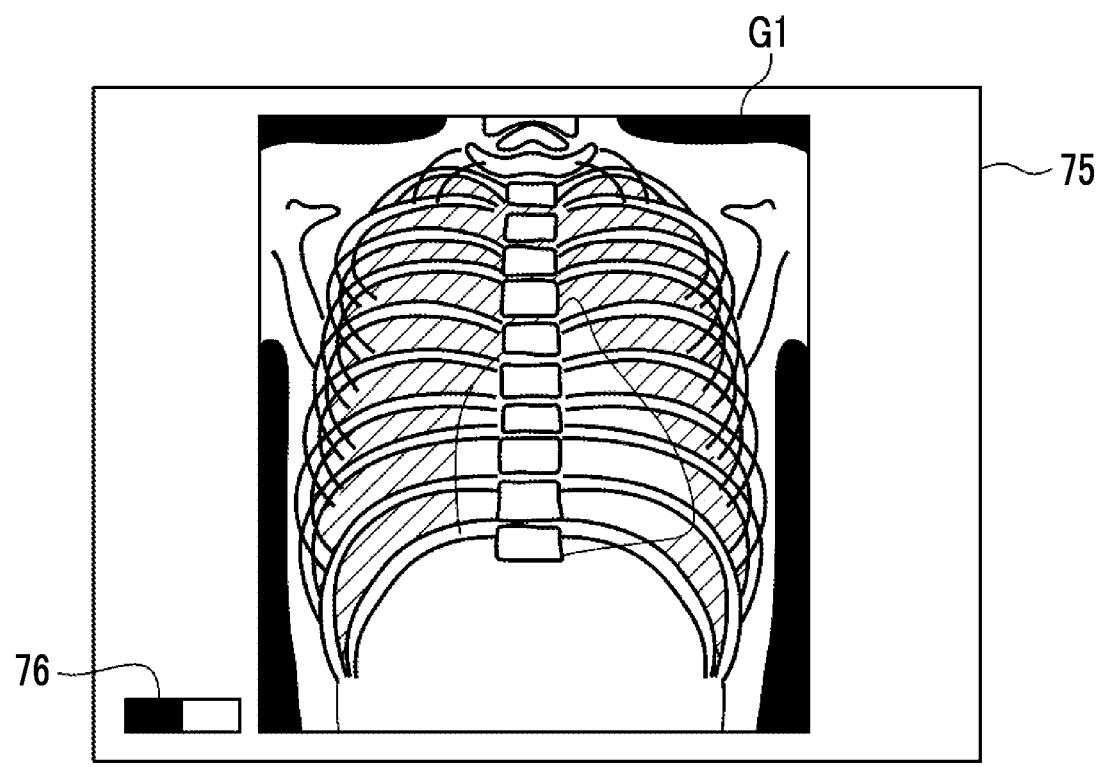
FIG. 14 is a diagram illustrating a processed radiographic image display screen.

FIG. 14 is a diagram illustrating a display screen for a processed radiographic image. As illustrated in FIG. 14, the processed radiographic image G1 is displayed on a display screen 75 for a processed radiographic image. Here, the process of detecting the region of the surgical tool requires a lot of time because the amount of calculation is large. Therefore, a progressive bar 76 indicating that the surgical tool detection process is being performed in the background is displayed on the display screen 75. The operator can know from the progressive bar 76 that the detection process is being performed in the background and the progress of the detection process. In a case in which the region of the surgical tool is included in the processed radiographic image G1, the displayed region of the surgical tool may be checked in the displayed processed radiographic image G1. However, in FIG. 14, the region of the surgical tool is not included in the processed radiographic image G1.

In a case in which the detection process ends, the display control unit 23 determines whether or not the region of the surgical tool has been detected from the radiographic image G0 (Step ST17). In a case in which the determination result in Step ST17 is "Yes", the display control unit 23 displays the processed radiographic image G1 in which the region of the surgical tool has been highlighted on the display unit 6 (Step ST18). Then, the process ends. On the other hand, in a case in which the determination result in Step ST17 is "No", the display control unit 23 notifies that the region of the surgical tool has not been detected (Step ST19). Then, the process ends.

Figure 15:
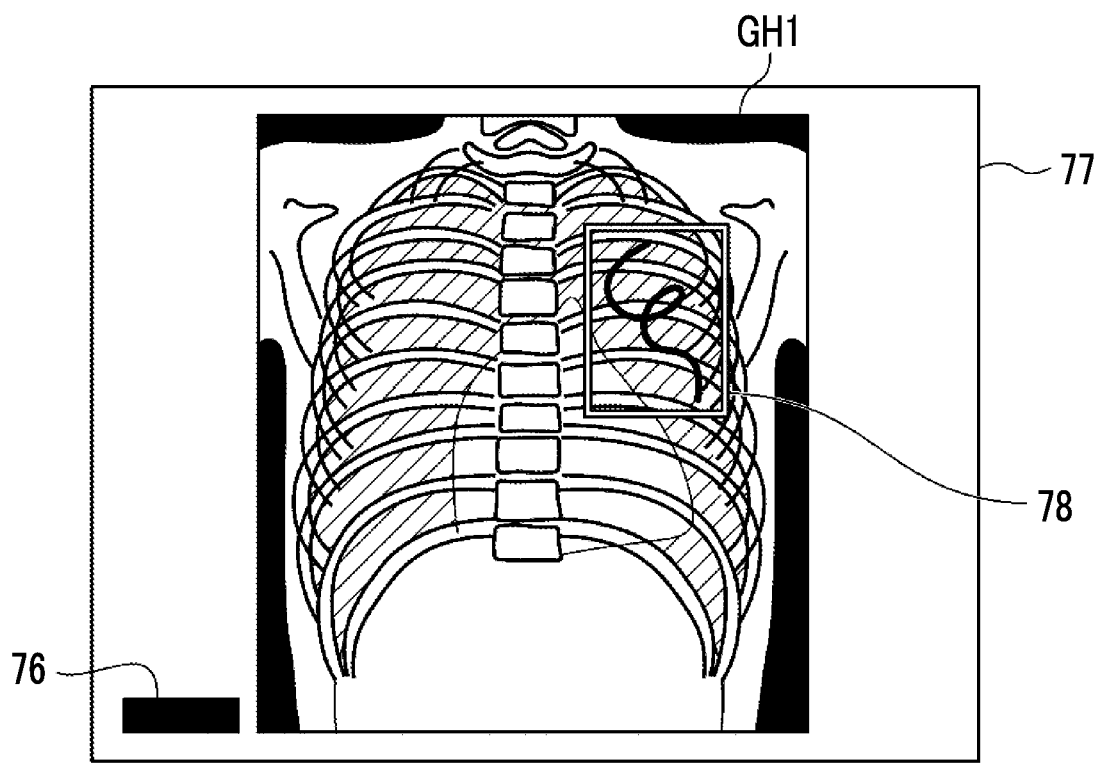
FIG. 15 is a diagram illustrating a display screen for a processed radiographic image in which a region of a surgical tool is highlighted.

FIG. 15 is a diagram illustrating a display screen for a processed radiographic image in which the region of the surgical tool has been highlighted. As illustrated in FIG. 15, a processed radiographic image GH1 obtained by adding a frame 78 to the detected region of the surgical tool in the processed radiographic image G1 to highlight the region of the surgical tool is displayed on a display screen 77. On the display screen 77, the progressive bar 76 indicates that the progress has been completed. In addition, instead of adding the frame 78, the region of the surgical tool may be masked or a mark may be added. Here, the processed radiographic image GH1 in which the region of the surgical tool has been highlighted may be displayed on the display unit 6 by superimposing the frame 78 or the like on the processed radiographic image G1. In addition, a process of adding a mask or the like may be performed on the processed radiographic image G1 to separately generate the processed radiographic image GH1 in which the region of the surgical tool has been highlighted and the processed radiographic image GH1 may be displayed on the display unit 6.

As described above, in the second embodiment, the image processing for checking a surgical tool is performed on the radiographic image G0 and the processed radiographic image G1 is displayed. Therefore, the region of the surgical tool can be easily checked by the processed radiographic image G1. Therefore, according to this embodiment, it is possible to reliably prevent a surgical tool from remaining in the body of the patient after surgery in combination with highlighting the region of the surgical tool.

In the second embodiment, the image processing for checking a surgical tool is performed on the radiographic image G0 in response to the surgical tool detection command. However, the present disclosure is not limited to thereto. The image processing for checking a surgical tool may be performed on the radiographic image G0 without waiting for the surgical tool detection command or in response to a command for only image processing.

Figure 16:
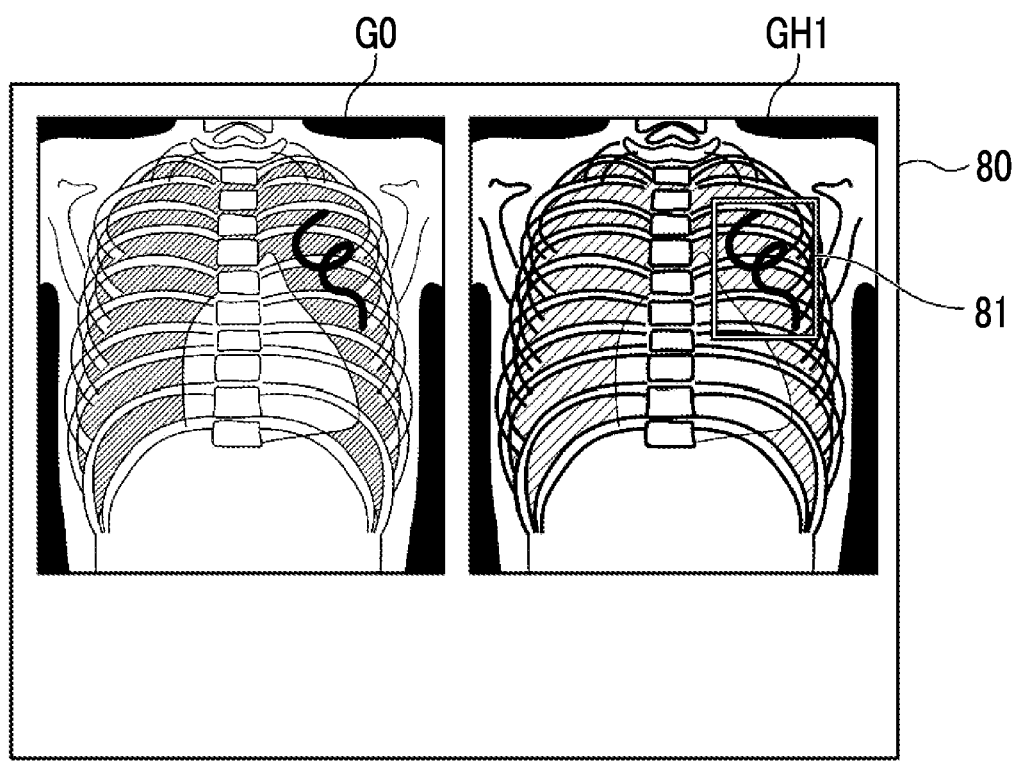
FIG. 16 is a diagram illustrating a display screen on which a radiographic image and a processed radiographic image are displayed together.

In the second embodiment, in a case in which the detection command is input, the processed radiographic image G1 and the processed radiographic image GH1 in which the region of the surgical tool has been highlighted are displayed on the display unit 6, instead of the radiographic image G0. However, the processed radiographic image G1 and the processed radiographic image GH1 in which the region of the surgical tool has been highlighted may be displayed on the display unit 6 together with the radiographic image G0. FIG. 16 is a diagram illustrating a display screen on which the radiographic image G0 and the processed radiographic image GH1 in which the region of the surgical tool has been highlighted are displayed together. FIG. 16 illustrates a display screen in a case in which the region of the surgical tool is detected from the processed radiographic image G1. As illustrated in FIG. 16, the radiographic image G0 and the processed radiographic image GH1 in which the region of the surgical tool has been highlighted are displayed on a display screen 80. In addition, FIG. 16 illustrates the processed radiographic image GH1 in which a frame 81 is added to the detected region of the surgical tool to highlight the region of the surgical tool. In FIG. 16, a frame or the like for highlighting the region of the surgical tool is not displayed in the radiographic image G0. However, the frame or the like for highlighting the region of the surgical tool may be added to the radiographic image G0. In addition, the frame or the like for highlighting the region of the surgical tool may be added only to the radiographic image G0. Further, image processing for display may be performed on the radiographic image G0.

Figure 17:
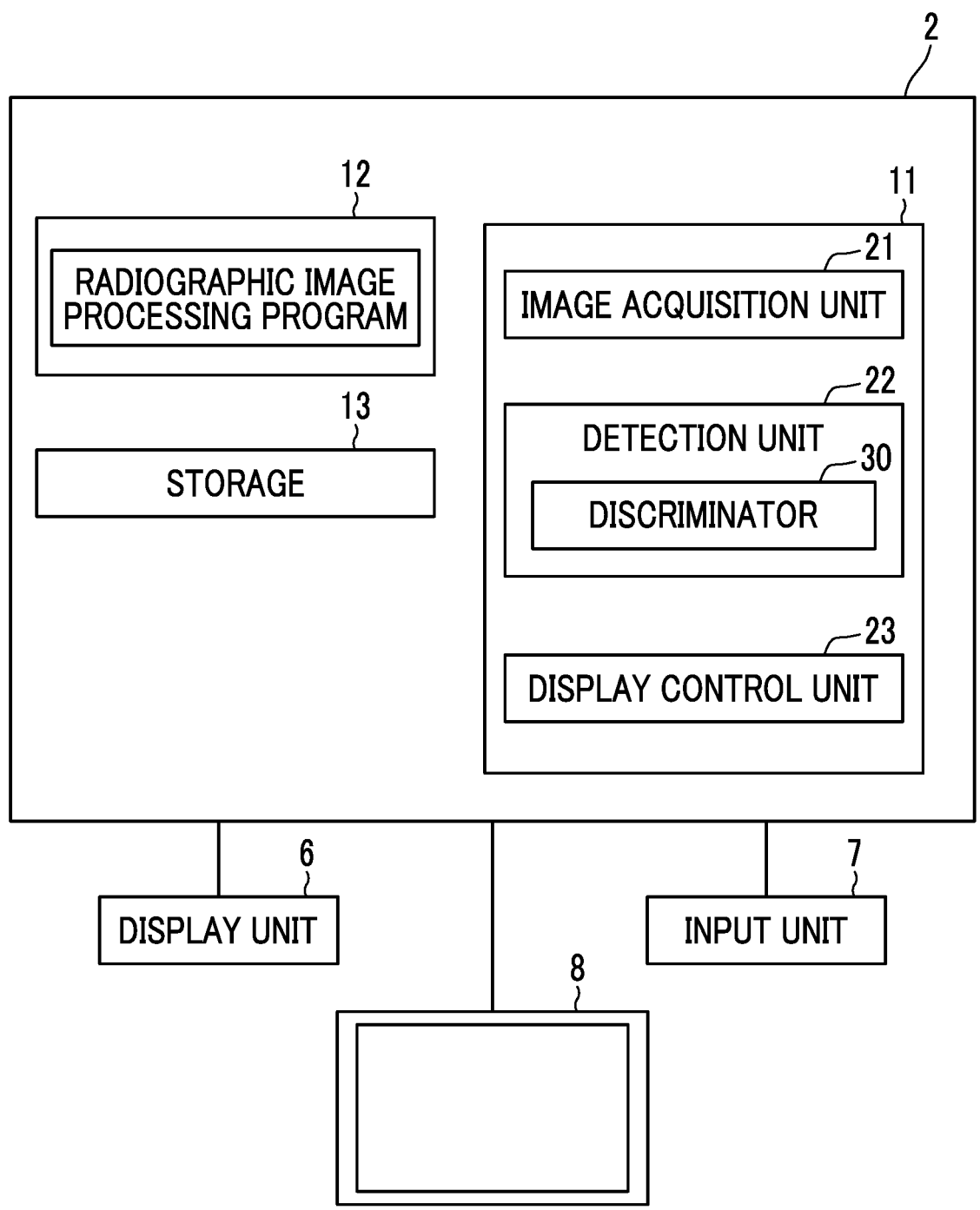
FIG. 17 is a diagram schematically illustrating a configuration of a radiographic image processing apparatus according to a third embodiment.

Next, a third embodiment of the present disclosure will be described. FIG. 17 is a diagram schematically illustrating the configuration of a radiographic image processing apparatus according to the third embodiment implemented by installing, for example, a radiographic image processing program according to the third embodiment in the console 2. In FIG. 17, the same components as those in FIG. 3 are denoted by the same reference numerals and the detailed description thereof will not be repeated. As illustrated in FIG. 17, the radiographic image processing apparatus according to the third embodiment differs from the radiographic image processing apparatus according to the first embodiment in that a display unit 8 having a larger screen and/or a higher resolution than the display unit 6 is connected to the console 2 and the radiographic image G0 is displayed on both the display unit 6 and the display unit 8.

The display unit 8 consists of, for example, a liquid crystal monitor and has a larger screen size than the display unit 6. For example, while the screen size of the display unit 6 is 14 to 15 inches, the screen size of the display unit 8 is 40 to 50 inches. The display unit 8 is attached to, for example, the wall of the operating room. The display unit 8 may have the same size as the display unit 6 or may have a higher resolution than the display unit 6. For example, in a case in which the resolution of the display unit 6 is 1 megapixel, the resolution of the display unit 8 may be 2 megapixels or 3 megapixels or more. The display unit 8 may have a larger size and higher resolution than the display unit 6.

Figure 18:
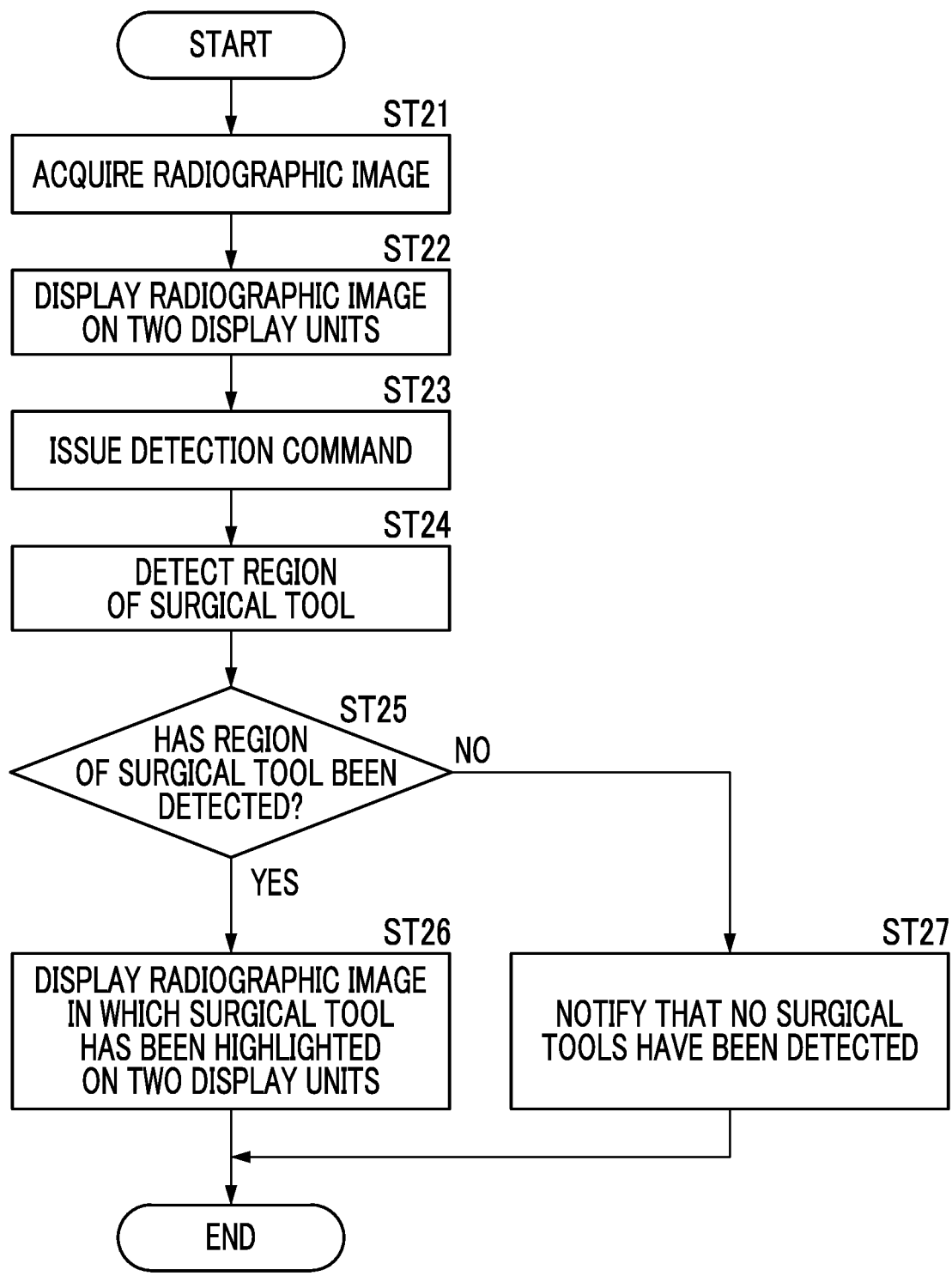
FIG. 18 is a flowchart illustrating a process performed in the third embodiment.

Next, a process performed in the third embodiment will be described. FIG. 18 is a flowchart illustrating the process performed in the third embodiment. First, the image acquisition unit 21 acquires the radiographic image G0 as a detection target (Step ST21) and the display control unit 23 displays the radiographic image G0 on each of the two display units 6 and 8 (Step ST22). The display screen 70 illustrated in FIG. 13 is displayed on the display unit 6. Further, the display screen 70 may also be displayed on the display unit 8 or only the radiographic image G0 may be displayed on the display unit 8. Further, image processing for display may be performed on the radiographic image G0.

Next, in a case in which the detection button 71 is selected and a surgical tool detection command is input from the input unit 7 (Step ST23), the detection unit 22 detects the region of the surgical tool from the radiographic image G0 (Step ST24). In this case, a progressive bar indicating the progress of the surgical tool detection process may be displayed on the display screen 70.

In a case in which the detection process ends, the display control unit 23 determines whether the region of the surgical tool has been detected from the radiographic image G0 (Step ST25). In a case in which the determination result in Step ST25 is "Yes", the display control unit 23 displays the radiographic image G0 in which the region of the surgical tool has been highlighted on the two display units 6 and 8 (Step ST26). Then, the process ends. On the other hand, in a case in which the determination result in Step ST25 is "No", the display control unit 23 notifies that the region of the surgical tool has not been detected (Step ST27). Then, the process ends. The notification may be displayed only on the display unit 6, may be displayed only on the display unit 8, or may be displayed on both the display unit 6 and the display unit 8.

As described above, in the third embodiment, the radiographic image G0 is displayed on the display unit 8 having a larger screen and/or a higher resolution than the display unit 6. Therefore, the region of the surgical tool can be easily checked by the radiographic image displayed on the display unit 8. Therefore, according to this embodiment, it is possible to reliably prevent a surgical tool from remaining in the body of the patient after surgery in combination with highlighting the region of the surgical tool.

Figure 19:
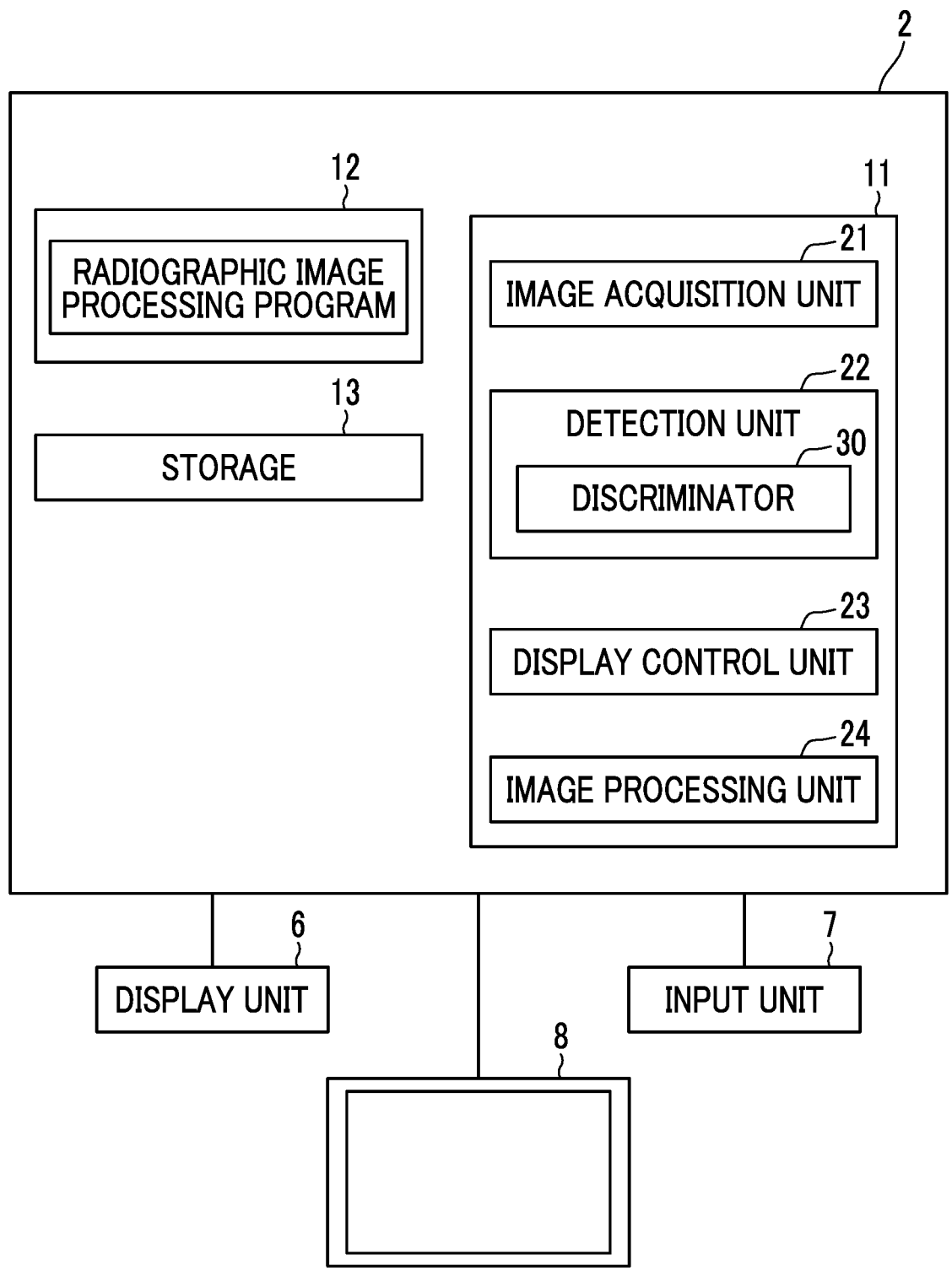
FIG. 19 is a diagram schematically illustrating a configuration of a radiographic image processing apparatus according to a fourth embodiment.

Next, a fourth embodiment of the present disclosure will be described. FIG. 19 is a diagram schematically illustrating the configuration of a radiographic image processing apparatus according to the fourth embodiment implemented by installing, for example, a radiographic image processing program according to the fourth embodiment in the console 2. In FIG. 19, the same components as those in FIG. 11 are denoted by the same reference numerals and the detailed description thereof will not be repeated. As illustrated in FIG. 19, the radiographic image processing apparatus according to the fourth embodiment differs from the radiographic image processing apparatus according to the second embodiment in that the display unit 8 having a larger screen and/or a higher resolution than the display unit 6 is connected to the console 2 and the radiographic image G0 and the processed radiographic image G1 are displayed on both the display unit 6 and the display unit 8.

Figure 20:
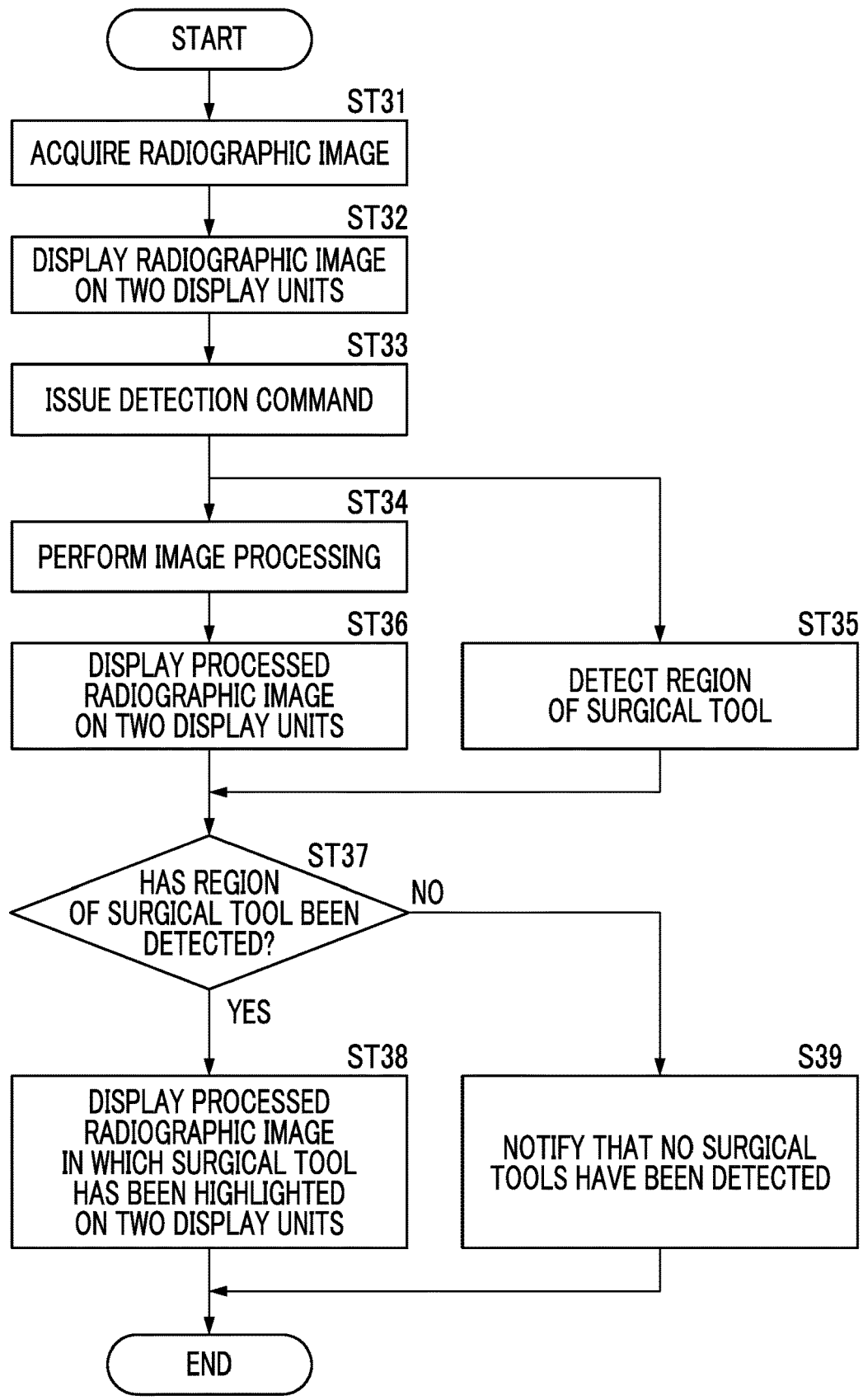
FIG. 20 is a flowchart illustrating a process performed in the fourth embodiment.
Figure 21:
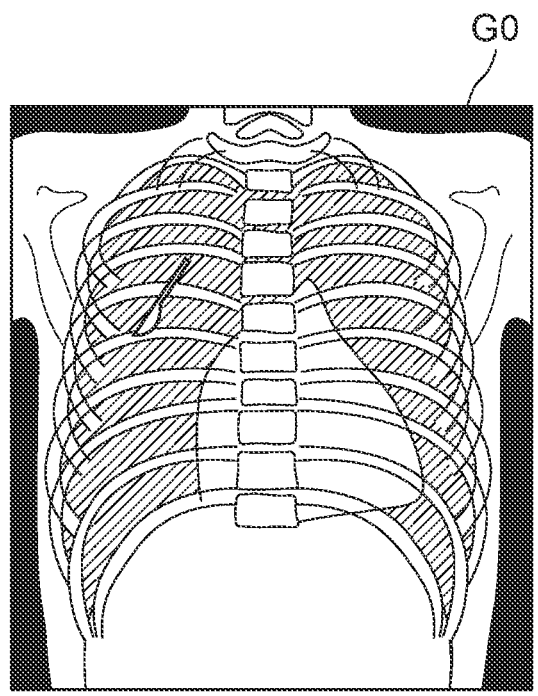
FIG. 21 is a diagram illustrating a radiographic image including a scalpel.
Figure 22:
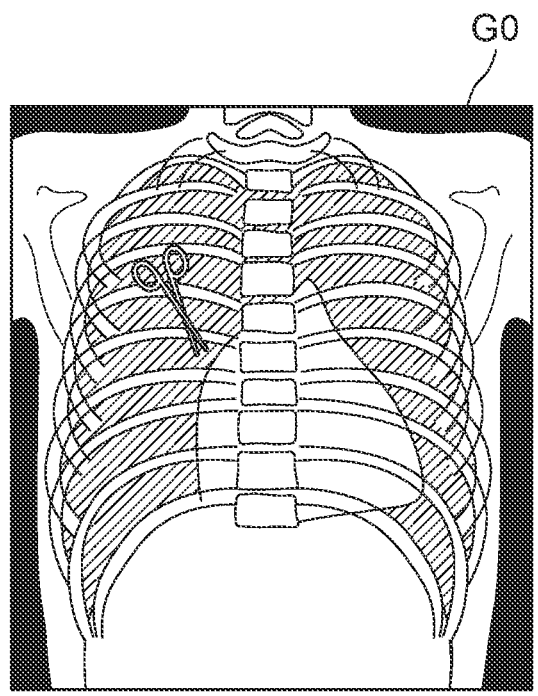
FIG. 22 is a diagram illustrating a radiographic image including scissors.
Figure 23:
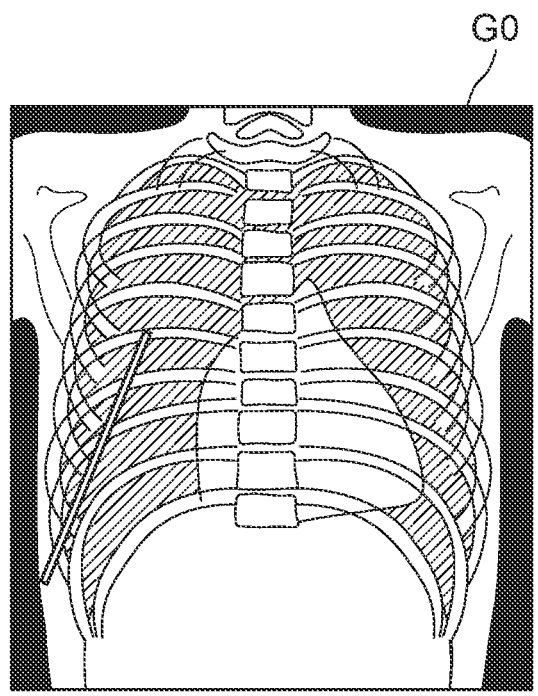
FIG. 23 is a diagram illustrating a radiographic image including a drain.
Figure 24:
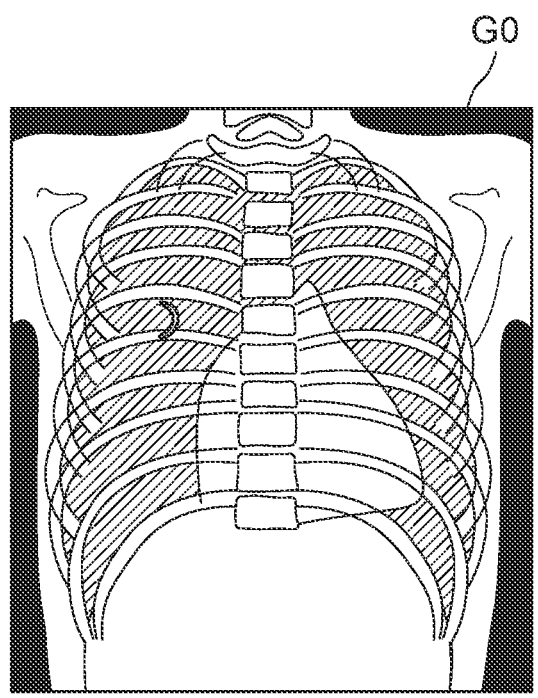
FIG. 24 is a diagram illustrating a radiographic image including a needle.
Figure 25:
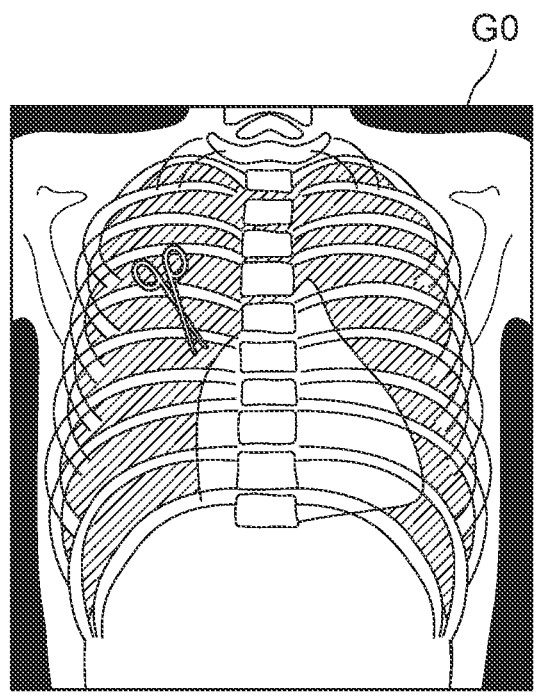
FIG. 25 is a diagram illustrating a radiographic image including forceps.

Next, a process performed in the fourth embodiment will be described. FIG. 20 is a flowchart illustrating the process performed in the fourth embodiment. The image acquisition unit 21 acquires the radiographic image G0 as a detection target (Step ST31) and the display control unit 23 displays the radiographic image G0 on the two display units 6 and 8 (Step ST32). Then, the display screen 70 illustrated in FIG. 13 is displayed on the display unit 6. The display screen 70 may also be displayed on the display unit 8 or only the radiographic image G0 may be displayed on the display unit 8. Further, image processing for display may be performed on the radiographic image G0.

Next, in a case in which the detection button 71 is selected and a surgical tool detection command is input from the input unit 7 (Step ST33), the image processing unit 24 performs image processing for checking a surgical tool on the radiographic image G0 (Step ST34). The detection unit 22 detects the region of the surgical tool from the radiographic image G0 in response to the detection command (Step ST35). Further, after the image processing for checking a surgical tool, the display control unit 23 displays the processed radiographic image G1 on the two display units 6 and 8 (Step ST36). Then, the display screen 75 illustrated in FIG. 14 is displayed on the display unit 6. The display screen 75 may also be displayed on the display unit 8 or only the processed radiographic image G1 may be displayed on the display unit 8. The process in Step ST35 is performed in parallel to the processes in Steps ST34 and ST36. However, the process in Step ST35 may be performed after Step ST34 or Step ST36. In a case in which the region of the surgical tool is detected from the processed radiographic image G1, the process in Step ST35 may be performed in parallel to the process in Step ST36 after Step ST34 or may be performed after Step ST36.

In a case in which the detection process ends, the display control unit 23 determines whether the region of the surgical tool has been detected from the radiographic image G0 (Step ST37). In a case in which the determination result in Step ST37 is "Yes", the display control unit 23 displays the processed radiographic image G1 in which the region of the surgical tool has been highlighted on the two display units 6 and 8 (Step ST38). Then, the process ends. On the other hand, in a case in which the determination result in Step ST37 is "No", the display control unit 23 notifies that the region of the surgical tool has not been detected (Step ST39). Then, the process ends. The notification may be displayed only on the display unit 6, may be displayed only on the display unit 8, or may be displayed on both the display unit 6 and the display unit 8.

As described above, in the fourth embodiment, the image processing for checking a surgical tool is performed on the radiographic image G0 to derive the processed radiographic image G1 and the processed radiographic image G1 is also displayed on the display unit 8 having a large screen and/or a high resolution. Therefore, the region of the surgical tool can be easily checked by the processed radiographic image GH1 in which the region of the surgical tool has been highlighted and which is displayed on the display unit 8. Therefore, according to this embodiment, it is possible to reliably prevent a surgical tool from remaining in the body of the patient after surgery in combination with highlighting the region of the surgical tool.

In the fourth embodiment, the image processing for checking a surgical tool is performed on the radiographic image G0 after the surgical tool detection command is input. However, the present disclosure is not limited thereto. The image processing for checking a surgical tool may be performed on the radiographic image G0 without waiting for the surgical tool detection command or in response to a command for only image processing.

Further, in the fourth embodiment, in a case in which the detection command is input, the processed radiographic image G1 is displayed on the display units 6 and 8, instead of the radiographic image G0. However, the radiographic image G0 and the processed radiographic image G1 may be displayed together on the display units 6 and 8.

In each of the above-described embodiments, the turn-on and turn-off of the highlight display of the radiographic image G0 and/or the processed radiographic image G1 may be switched in response to a command from the input unit 7.

Further, in the above-described embodiments, the radiographic image G0 and/or the processed radiographic image G1 in which the region of the surgical tool has been detected may be transmitted to an external apparatus such as the PACS 101. In this case, information indicating that the region of the surgical tool has been detected may be given to the radiographic image G0 and/or the processed radiographic image G1. For example, in a protocol such as digital imaging and communication in medicine (DICOM) that defines the storage format of image data and communication between apparatuses, various kinds of information may be given as accessory information to the radiographic image G0 and/or the processed radiographic image G1. Therefore, the DICOM protocol may be used to give information indicating that the region of the surgical tool has been detected to the accessory information of the radiographic image G0 and/or the processed radiographic image G1. Further, a process of adding a frame or the like for highlighting the region of the surgical tool may be performed on the radiographic image G0 and/or the processed radiographic image G1 to generate the radiographic image GH0 and/or the processed radiographic image GH1 in which the region of the surgical tool has been highlighted and the generated radiographic image GH0 and/or processed radiographic image GH1 may be transmitted to an external apparatus.

Further, in each of the above-described embodiments, the console 2 performs, for example, the surgical tool detection process and the image processing. However, the present disclosure is not limited thereto. For example, the radiographic image processing program according to each of the embodiments of the present disclosure may be installed in the PACS 101 illustrated in FIG. 2. The radiographic image G0 acquired by the console 2 may be transmitted to the PACS 101 and the PACS 101 may perform a process of detecting the region of the surgical tool from the radiographic image G0 or may perform image processing for checking a surgical tool. In this case, the PACS 101 may perform the process of adding a frame or the like for highlighting the region of the surgical tool on the radiographic image G0 and/or the processed radiographic image G1 to generate the radiographic image GH0 and/or the processed radiographic image GH1 in which the region of the surgical tool has been highlighted and transmit the generated radiographic image GH0 and/or processed radiographic image GH1 to the console 2. Further, the PACS 101 may give information indicating that the region of the surgical tool has been detected to the accessory information of the radiographic image G0 and/or the processed radiographic image G1 and transmit the accessory information to the console 2, using the DICOM protocol. In this case, the console 2 performs the process of highlighting the region of the surgical tool included in the radiographic image G0 and/or the processed radiographic image G1 on the basis of the accessory information and displays the radiographic image GH0 and/or the processed radiographic image GH1 in which the region of the surgical tool has been highlighted on the display units 6 and 8. In this case, it is possible to switch the turn-on and turn-off of the highlight display.

Further, in the second and fourth embodiments, the degree of image processing for the displayed processed radiographic image G1 may be changed. For example, the degree of emphasis of the sharpness and the degree of change of the gradation of the processed radiographic image G1 may be changed. In this case, it is possible to display the processed radiographic image G1 with the desired quality on the display unit 6 and/or the display unit 8.

Further, in each of the above-described embodiments, the detection unit 22 detects the region of the surgical tool using the discriminator 30. However, the present disclosure is not limited thereto. A histogram of the radiographic image G0 may be calculated and it may be determined whether or not a signal value of the surgical tool is included in the histogram to detect the region of the surgical tool from the radiographic image G0 or the processed radiographic image G1.

In each of the above-described embodiments, the radiographic image G0 is a still image. However, the present disclosure is not limited thereto. The radiographic image G0 may be a moving image. In this case, the process of detecting the region of the surgical tool is performed on each frame of the radiographic image G0 which is a moving image.

In each of the above-described embodiments, the radiographic image G0 of the subject H is acquired by the radiation source 4 and the radiation detector 5. However, the present disclosure is not limited thereto. For example, in some cases, the operator performs surgery while observing the radiographic image G0 of the patient using a C-arm fluoroscopic apparatus. In this case, the radiographic image G0 may be acquired by the C-arm fluoroscopic apparatus.

In the above-described embodiments, the gauze 40 as a surgical tool is a detection target. However, the present disclosure is not limited thereto. Any surgical tools, such as a scalpel, scissors, a drain, a needle, a thread, and forceps, which are used during surgery and should not remain in the body may be used as the detection targets. In this case, the discriminator 30 may be trained so as to discriminate the target surgical tool. The discriminator 30 is trained so as to detect a plurality of channels, which makes it possible to construct the discriminator 30 so as to discriminate not only one kind of surgical tool but also a plurality of kinds of surgical tools.

In addition, in the above-described embodiments, the radiation is not particularly limited. For example, $\alpha$-rays and $\gamma$-rays other than X-rays can be applied.

In the above-described embodiments, for example, the following various processors can be used as a hardware structure of processing units performing various processes, such as the image acquisition unit 21, the detection unit 22, the display control unit 23, and the image processing unit 24. The various processors include, for example, a CPU which is a general-purpose processor executing software (program) to function as various processing units, a programmable logic device (PLD), such as a field programmable gate array (FPGA), which is a processor whose circuit configuration can be changed after manufacture, and a dedicated electric circuit, such as an application-specific integrated circuit (ASIC), which is a processor having a dedicated circuit configuration designed to perform a specific process.

One processing unit may be configured by one of the various processors or a combination of two or more processors of the same type or different types (for example, a combination of a plurality of FPGAs or a combination of a CPU and an FPGA). Further, a plurality of processing units may be configured by one processor.

A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system-on-chip (SoC). As such, various processing units are configured by using one or more of the various processors as the hardware structure.

Furthermore, specifically, an electric circuit (circuitry) obtained by combining circuit elements, such as semiconductor elements, can be used as the hardware structure of the various processors.

What is claimed is:

1. A radiographic image processing apparatus comprising at least one processor, wherein the processor is configured to:
   detect a region of a surgical tool in a radiographic image of a patient;
   in a case in which the surgical tool is detected, display the radiographic image in which the detected region of the surgical tool has been highlighted on a display;
   perform image processing for checking the surgical tool on the radiographic image to derive a processed radiographic image,
   display, on the display, the radiographic image before the image processing for checking the surgical tool,
   derive the processed radiographic image and the start a process of detecting the region of the surgical tool in response to a command to detect the region of the surgical tool,
   in a case in which the processed radiographic image is derived, display the processed radiographic image on the display, instead of the radiographic image before the image processing or together with the radiographic image before the image processing, and
   after the process of detecting the region of the surgical tool ends, display the radiographic image in which the region of the surgical tool has been highlighted on the display.

2. The radiographic image processing apparatus according to claim 1,
   wherein the radiographic image in which the detected region of the surgical tool has been highlighted and which is displayed on the display is the processed radiographic image.

3. The radiographic image processing apparatus according to claim 1,
   wherein the processor is configured to display the radiographic image in which the detected region of the surgical tool has been highlighted on another display that has a larger size and/or a higher resolution than the display.

4. The radiographic image processing apparatus according to claim 1,
   wherein the processor is configured to display the radiographic image before the image processing, the processed radiographic image, and the radiographic image in which the detected region of the surgical tool has been highlighted on another display that has a larger size and/or a higher resolution than the display.

5. The radiographic image processing apparatus according to claim 1,
   wherein the processor is configured to, in a case in which the surgical tool is not detected, notify the fact.

6. The radiographic image processing apparatus according to claim 1,
   wherein the radiographic image is acquired by a portable radiation detector or an imaging apparatus that is installed in an operating room for performing surgery on the patient.

7. The radiographic image processing apparatus according to claim 1,
   wherein the processor is configured to discriminate the region of the surgical tool in an input radiographic image by a discriminator trained so as to discriminate the region of the surgical tool in the input radiographic image.

8. The radiographic image processing apparatus according to claim 1,
   wherein the surgical tool includes at least one of gauze, a scalpel, scissors, a drain, a needle, a thread, or forceps.

9. The radiographic image processing apparatus according to claim 8,
   wherein at least a portion of the gauze includes a radiation absorbing thread.

10. A radiographic image processing method comprising:
    detecting a region of a surgical tool in a radiographic image of a patient;
    in a case in which the surgical tool is detected, displaying the radiographic image on a display such that the detected region of the surgical tool is highlighted;
    performing image processing for checking the surgical tool on the radiographic image to derive a processed radiographic image,
    displaying, on the display, the radiographic image before the image processing for checking the surgical tool,
    deriving the processed radiographic image and the start a process of detecting the region of the surgical tool in response to a command to detect the region of the surgical tool,
    in a case in which the processed radiographic image is derived, displaying the processed radiographic image on the display, instead of the radiographic image before the image processing or together with the radiographic image before the image processing, and
    after the process of detecting the region of the surgical tool ends, displaying the radiographic image in which the region of the surgical tool has been highlighted on the display.

11. A non-transitory computer-readable storage medium that stores a radiographic image processing program that causes a computer to perform:
    detecting a region of a surgical tool in a radiographic image of a patient;
    in a case in which the surgical tool is detected, displaying the radiographic image on a display such that the detected region of the surgical tool is highlighted;
    performing image processing for checking the surgical tool on the radiographic image to derive a processed radiographic image,
    displaying, on the display, the radiographic image before the image processing for checking the surgical tool,
    deriving the processed radiographic image and the start a process of detecting the region of the surgical tool in response to a command to detect the region of the surgical tool,
    in a case in which the processed radiographic image is derived, displaying the processed radiographic image on the display, instead of the radiographic image before the image processing or together with the radiographic image before the image processing, and
    after the process of detecting the region of the surgical tool ends, displaying the radiographic image in which the region of the surgical tool has been highlighted on the display.

* * * * *